(12) United States Patent
Ishikawa et al.

(10) Patent No.: US 11,360,089 B2
(45) Date of Patent: Jun. 14, 2022

(54) IMMUNOLOGICAL TEST APPARATUS AND OPERATION METHOD THEREOF, INFORMATION PROCESSING APPARATUS AND OPERATION METHOD THEREOF, AND INFORMATION PROCESSING SYSTEM

(71) Applicant: FUJIFILM Corporation, Tokyo (JP)

(72) Inventors: Shigetoshi Ishikawa, Kanagawa (JP); Yoshinari Oda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 16/541,153

(22) Filed: Aug. 15, 2019

(65) Prior Publication Data

US 2019/0369094 A1 Dec. 5, 2019

Related U.S. Application Data

(63) Continuation of application No. PCT/JP2018/002832, filed on Jan. 30, 2018.

(30) Foreign Application Priority Data

Feb. 15, 2017 (JP) .............................. JP2017-025852

(51) Int. Cl.
  *G01N 33/569* (2006.01)
  *G16H 50/80* (2018.01)
  *G16B 45/00* (2019.01)

(52) U.S. Cl.
  CPC ....... *G01N 33/56983* (2013.01); *G16B 45/00* (2019.02); *G16H 50/80* (2018.01); *G01N 2469/10* (2013.01); *G01N 2800/26* (2013.01); *G01N 2800/56* (2013.01)

(58) Field of Classification Search
  CPC .............................................. G01N 33/56983
  See application file for complete search history.

(56) References Cited

U.S. PATENT DOCUMENTS

| 8,423,379 | B2 | 4/2013 | Oda et al. |
| 9,460,263 | B2 | 10/2016 | Holmes et al. |
| 11,139,084 | B2 | 10/2021 | Holmes et al. |
| 11,158,429 | B2 | 10/2021 | Holmes et al. |
| 11,195,624 | B2 | 12/2021 | Holmes et al. |
| 2004/0121334 | A1 | 6/2004 | Wei et al. |
| 2008/0254441 | A1 | 10/2008 | Mohammed |
| 2009/0093968 | A1 | 4/2009 | Kawamata et al. |
| 2009/0246861 | A1 | 10/2009 | Manabe |
| 2010/0029503 | A1 | 2/2010 | Nomura et al. |
| 2010/0087010 | A1 | 4/2010 | Yamauchi |
| 2011/0093249 | A1 | 4/2011 | Holmes et al. |
| 2013/0203043 | A1 | 8/2013 | Ozcan et al. |
| 2014/0273189 | A1 | 9/2014 | Ma et al. |

FOREIGN PATENT DOCUMENTS

| CN | 101668473 | 3/2010 |
| CN | 102713914 | 10/2012 |
| JP | 2008522169 | 6/2008 |
| JP | 2009236685 | 10/2009 |
| JP | 2009277176 | 11/2009 |
| JP | 2011209036 | 10/2011 |
| JP | 2012103150 | 5/2012 |
| JP | 5012507 | 8/2012 |
| JP | 2013076711 | 4/2013 |
| JP | 2014016261 | 1/2014 |
| JP | 2014532869 | 12/2014 |
| JP | 2015010943 | 1/2015 |
| WO | 2008090922 | 7/2008 |

OTHER PUBLICATIONS

"International Search Report (Form PCT/ISA/210) of PCT/JP2018/002832," dated Mar. 20, 2018, with English translation thereof, pp. 1-5.
"Written Opinion of the International Searching Authority (Form PCT/ISA/237) of PCT/JP2018/002832," dated Mar. 20, 2018, with English translation thereof, pp. 1-7.
"Office action of Europe Counterpart Application", dated Aug. 4, 2021, p. 1-p. 7.
"Search Report of Europe Counterpart Application No. 18754791.4", which publication number is EP3584579, dated Feb. 13, 2020, p. 1-p. 11.
"Office Action of China Counterpart Application" with English translation thereof, dated Jan. 7, 2022, p. 1-p. 16.

*Primary Examiner* — Albert M Navarro
*Assistant Examiner* — Mark Navarro
(74) *Attorney, Agent, or Firm* — JCIPRNET

(57) ABSTRACT

A main controller of an immunological test apparatus counts an elapsed time TP. An information output unit outputs required determination time information regarding a required determination time so as to be associated with information of a determination result. The required determination time information is at least information indicating that the elapsed time TP exceeds a set time TS at which sensitization processing, in which a chemical solution for sensitizing the coloration state of a reagent that is combined with influenza virus to be colored is spread onto a carrier, is started, that is, information indicating that the sensitization processing has been performed.

7 Claims, 21 Drawing Sheets

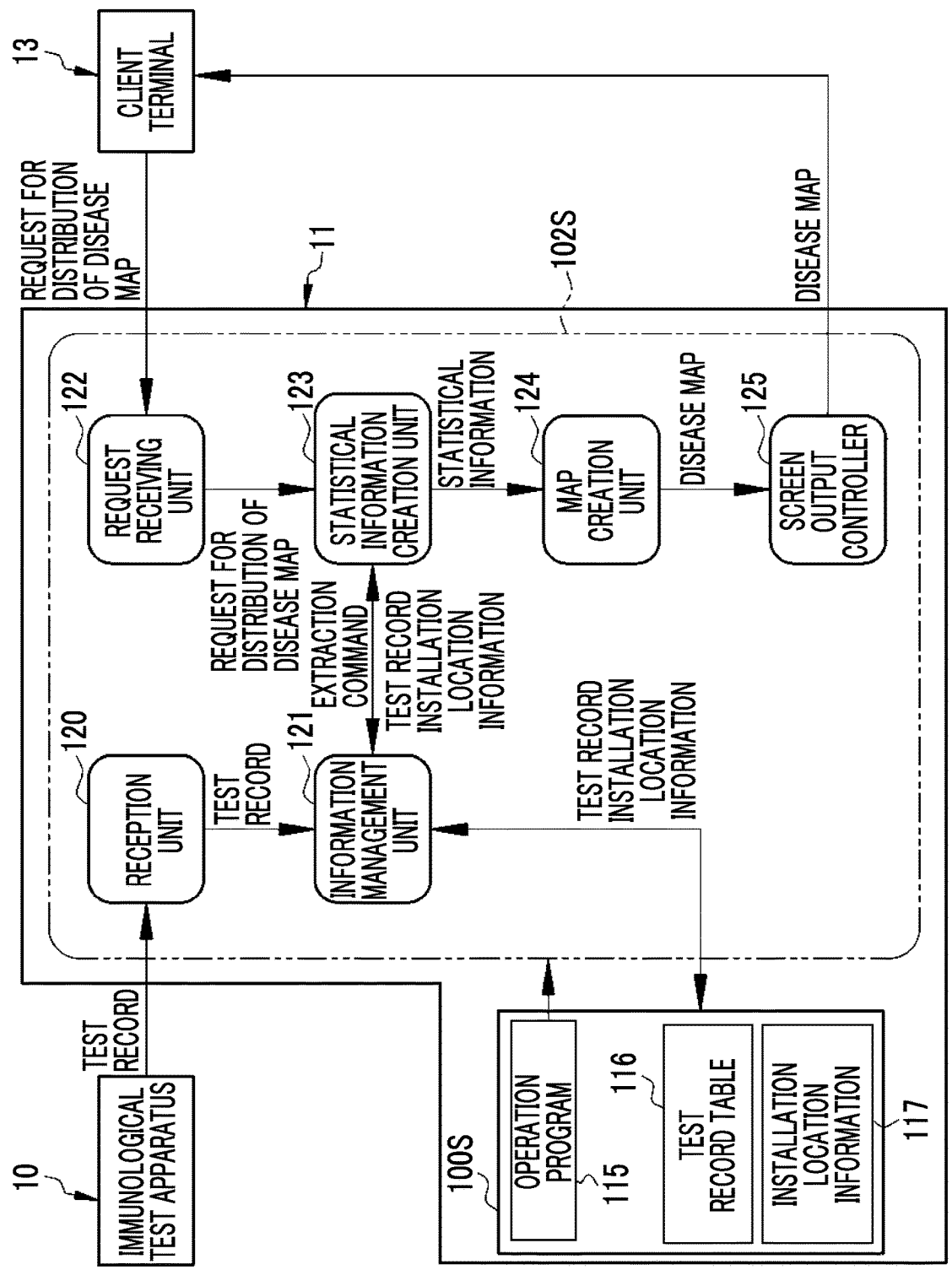

FIG. 14

| RECEPTION DATE AND TIME | APPARATUS ID | DETERMINATION RESULT INFORMATION |
|---|---|---|
| ⋮ | ⋮ | ⋮ |
| 01.31.2017 10:00 | IMM001 | A TYPE INFLUENZA POSITIVE |
| 01.31.2017 10:00 | IMM002 | A TYPE INFLUENZA POSITIVE |
| 01.31.2017 10:05 | IMM003 | B TYPE INFLUENZA POSITIVE |
| 01.31.2017 10:10 | IMM008 | A TYPE INFLUENZA POSITIVE<br>B TYPE INFLUENZA POSITIVE |
| 01.31.2017 10:20 | IMM010 | A TYPE INFLUENZA POSITIVE |
| ⋮ | ⋮ | ⋮ |

FIG. 15

| RECEPTION DATE AND TIME | APPARATUS ID | DETERMINATION RESULT INFORMATION | REQUIRED DETERMINATION TIME INFORMATION |
|---|---|---|---|
| ⋮ | ⋮ | ⋮ | ⋮ |
| 01.31.2017 09:30 | IMM100 | A TYPE INFLUENZA POSITIVE | SENSITIZATION PROCESSING EXECUTION |
| 01.31.2017 09:40 | IMM111 | A TYPE INFLUENZA POSITIVE | SENSITIZATION PROCESSING EXECUTION |
| 01.31.2017 10:00 | IMM115 | B TYPE INFLUENZA POSITIVE | SENSITIZATION PROCESSING EXECUTION |
| 01.31.2017 10:15 | IMM200 | A TYPE INFLUENZA POSITIVE | SENSITIZATION PROCESSING EXECUTION |
| 01.31.2017 10:15 | IMM222 | B TYPE INFLUENZA POSITIVE | SENSITIZATION PROCESSING EXECUTION |
| 01.31.2017 10:20 | IMM250 | A TYPE INFLUENZA POSITIVE | SENSITIZATION PROCESSING EXECUTION |
| ⋮ | ⋮ | ⋮ | ⋮ |

| APPARATUS ID | INSTALLATION LOCATION (ADDRESS OF MEDICAL INSTITUTION WHERE APPARATUS IS INSTALLED) |
|---|---|
| IMM001 | KITAOTSUKA, TOSHIMA-KU, TOKYO··· |
| IMM002 | KITAOTSUKA, TOSHIMA-KU, TOKYO··· |
| IMM003 | SHIRAYAMA, BUNKYO-KU, TOKYO··· |
| IMM004 | SHIRAYAMA, BUNKYO-KU, TOKYO··· |
| IMM005 | MINAMI-TORIYAMA, SETAGAYA-KU, TOKYO··· |
| ⋮ | ⋮ |
| IMM100 | KAWAGOE CITY, SAITAMA PREFECTURE··· |
| ⋮ | ⋮ |

| AREA (PREFECTURE) | NUMBER OF FIRST TEST RECORDS (NUMBER OF MIDDLE STAGE PATIENTS) |
|---|---|
| ⋮ | ⋮ |
| SAITAMA | 4000 |
| CHIBA | 100 |
| TOKYO | 3800 |
| KANAGAWA | 2900 |
| ⋮ | ⋮ |

| AREA (PREFECTURE) | NUMBER OF SECOND TEST RECORDS (NUMBER OF EARLY STAGE PATIENTS) |
|---|---|
| ⋮ | ⋮ |
| SAITAMA | 1500 |
| CHIBA | 500 |
| TOKYO | 5500 |
| KANAGAWA | 3100 |
| ⋮ | ⋮ |

| STATISTICAL INFORMATION DISPLAY SCREEN | | |
|---|---|---|
| AREA (PREFECTURE) | NUMBER OF MIDDLE STAGE PATIENTS | NUMBER OF EARLY STAGE PATIENTS |
| SAITAMA | 4000 | 1500 |
| CHIBA | 100 | 500 |
| TOKYO | 3800 | 5500 |
| KANAGAWA | 2900 | 3100 |
| WHOLE COUNTRY | 79800 | 62000 |

FIG. 28

| AREA | NUMBER OF MIDDLE STAGE PATIENTS | NUMBER OF EARLY STAGE PATIENTS |
|---|---|---|
| MINAMI ASHIGARA | MEDIUM | LARGE |
| KANAGAWA | MEDIUM | MEDIUM |
| KANTO REGION | MEDIUM | SMALL |
| WHOLE COUNTRY | SMALL | SMALL |

STATISTICAL INFORMATION DISPLAY SCREEN (160)

130

IMMUNOLOGICAL TEST APPARATUS AND OPERATION METHOD THEREOF, INFORMATION PROCESSING APPARATUS AND OPERATION METHOD THEREOF, AND INFORMATION PROCESSING SYSTEM

CROSS-REFERENCE TO RELATED APPLICATIONS

This application is a Continuation of PCT International Application No. PCT/JP2018/002832 filed on 30 Jan. 2018, which claims priority under 35 U.S.C § 119(a) to Japanese Patent Application No. 2017-025852 filed on 15 Feb. 2017. The above application is hereby expressly incorporated by reference, in its entirety, into the present application.

BACKGROUND OF THE INVENTION

1. Field of the Invention

The present invention relates to an immunological test apparatus and an operation method thereof, an information processing apparatus and an operation method thereof, and an information processing system.

2. Description of the Related Art

In recent years, in the medical field, an immunological test apparatus is widely used (for example, refer to JP2012-103150A). The immunological test apparatus can easily and quickly perform a qualitative reaction test for testing positive and negative of an infectious disease, such as influenza. In the immunological test apparatus, a carrier holding a reagent (antibody) that is combined with a test substance (antigen) to be colored is used. A sample for determining whether or not a test substance is present, for example, a sample in which a body fluid such as pharyngeal swab or nasal swab is mixed with a predetermined solution, is dropped onto the carrier.

The immunological test apparatus receives the carrier having a sample dropped thereon, images a portion of the reagent with an imaging element, and measures the coloration state (density, chromaticity) of the reagent based on an imaging signal obtained by the imaging. Then, it is determined whether or not the test substance is present in the sample based on the measurement result, and the determination result is displayed for a user, such as a medical staff member.

On the other hand, creating a disease map by expressing the number of patients with infectious diseases for each area on a map based on the statistical information of patients with infectious diseases and displaying the created disease map have been performed. For example, JP2009-277176A discloses an information processing system in which a measurement apparatus, an information processing apparatus (management server), and a client terminal are connected to each other through a network. The measurement apparatus is a thermometer, a sphygmomanometer, an imaging apparatus, a sample test apparatus, or the like, and transmits measured biological information to the information processing apparatus. The information processing apparatus calculates the number of patients with infectious diseases for each area, as statistical information, based on the biological information from the measurement apparatus and the installation location information of the measurement apparatus, and transmits the calculated number to a client terminal. The client terminal creates a disease map based on the number of patients with infectious diseases for each area from the server, and displays the disease map on a display unit.

SUMMARY OF THE INVENTION

Patients suffering from infectious diseases include patients with relatively mild symptoms at the early stage of infection (hereinafter, referred to as early stage patients) and patients with remarkable symptoms at the middle stage of infection (hereinafter, referred to as middle stage patients). The amount of test substance is relatively large in the case of middle stage patients but relatively small in the case of early stage patients. For this reason, in the immunological test apparatus, in the case of early stage patients, it takes a longer time to obtain a determination result indicating that a test substance is present in the sample than in the case of middle stage patients. Therefore, in the immunological test apparatus, it can be thought that the early stage patients and the middle stage patients can be distinguished from each other by referring to the elapsed time (hereinafter, referred to as required determination time) of a test taken until a determination result indicating that a test substance is present in the sample is obtained from the start of the test.

Once the early stage patients and the middle stage patients are distinguished from each other, the disease map can also be divided into a disease map relevant to the early stage patients and a disease map relevant to the middle stage patients. In particular, according to the disease map relevant to the former early stage patients, at the early stage of infection, it is possible to predict how the epidemic situation of the infectious disease changes from then on. Therefore, it can be thought that effective measures can be taken to prevent the spread of infection. However, JP2012-103150A and JP2009-277176A do not disclose that the required determination time is effectively used to prevent the spread of infection.

It is an object of the present invention to provide an immunological test apparatus and an operation method thereof, an information processing apparatus and an operation method and an operation program thereof, and an information processing system capable of effectively using a required determination time, which is the elapsed time of a test taken until a determination result indicating that a test substance is present in a sample is obtained from the start of the test, to prevent the spread of infection.

In order to solve the aforementioned problems, an immunological test apparatus of the present invention is an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement. The immunological test apparatus comprises: a timing unit that counts an elapsed time from start of a test; and an information output unit that outputs required determination time information regarding a required determination time, which is the elapsed time taken until a determination result indicating that the test substance is present in the sample is obtained, so as to be associated with information of the determination result.

It is preferable to further comprise: a chemical solution spreading unit that performs sensitization processing in which a chemical solution for sensitizing the coloration state is spread onto the carrier; and a driving controller that controls driving of the chemical solution spreading unit. It is preferable that, in a case where a determination result indicating that the test substance is present in the sample is not obtained during a period from the start of the test to a set time set in advance, the driving controller drives the chemical solution spreading unit to start the sensitization processing and that the information output unit outputs, as the required determination time information, at least information indicating that the elapsed time exceeds the set time.

It is preferable that the information output unit outputs the required determination time information only in a case where the elapsed time exceeds the set time and the sensitization processing is performed.

It is preferable that the information indicating that the elapsed time exceeds the set time is information indicating that the sensitization processing has been performed.

It is preferable that the information output unit transmits the required determination time information and the determination result information to an information processing apparatus connected through a network. It is preferable that the information output unit transmits the required determination time information and the determination result information for each test.

An operation method of an immunological test apparatus of the present invention is an operation method of an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement. The operation method comprises: a timing step of counting an elapsed time from start of a test; and an information output step of outputting required determination time information regarding a required determination time, which is the elapsed time taken until a determination result indicating that the test substance is present in the sample is obtained, so as to be associated with information of the determination result.

An information processing apparatus of the present invention is an information processing apparatus connected, through a network, to an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement. The information processing apparatus comprises: a reception unit that receives required determination time information regarding a required determination time, which is an elapsed time of a test taken until a determination result indicating that the test substance is present in the sample is obtained from start of the test, and information of the determination result from the immunological test apparatus through the network; and a statistical information creation unit that creates statistical information of early stage patients, who are patients at an early stage of infection of an infectious disease, based on the required determination time information, the determination result information, and installation location information regarding an installation location of the immunological test apparatus.

It is preferable to further comprise a map creation unit that creates a disease map by expressing the number of early stage patients of an infectious disease for each area on a map based on the statistical information. It is preferable that the statistical information creation unit also creates statistical information of middle stage patients who are patients at a middle stage of infection of an infectious disease and that the map creation unit also creates a disease map by expressing the number of middle stage patients of an infectious disease for each area on a map based on the statistical information of middle stage patients. It is preferable to further comprise an output controller that performs output control of the statistical information or the disease map.

An operation method of an information processing apparatus of the present invention is an operation method of an information processing apparatus connected, through a network, to an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement. The operation method comprises: a reception step of receiving required determination time information regarding a required determination time, which is an elapsed time of a test taken until a determination result indicating that the test substance is present in the sample is obtained from start of the test, and information of the determination result from the immunological test apparatus through the network; and a statistical information creation step of creating statistical information of early stage patients, who are patients at an early stage of infection of an infectious disease, based on the required determination time information, the determination result information, and installation location information regarding an installation location of the immunological test apparatus.

An information processing system of the present invention is an formation processing system comprises: an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement; and an information processing apparatus connected to the immunological test apparatus through a network. The immunological test apparatus has: a timing unit that counts an elapsed time from start of a test; and an information output unit that transmits required determination time information regarding a required determination time, which is the elapsed time taken until a determination result indicating that the test substance is present in the sample is obtained, to the information processing apparatus through the network so as to be associated with information of the determination result. The information processing apparatus has: a reception unit that receives the required determination time information and the determination result information from the immunological test apparatus; and a statistical information creation unit that creates statistical information of early stage patients, who are patients at an early stage of infection of an infectious disease, based on the required determination time information, the determination result information, and installation location information regarding an installation location of the immunological test apparatus.

According to the present invention, since the required determination time information regarding the required determination time, which is the elapsed time of a test taken until the determination result indicating that a test substance is present in a sample is obtained from the start of the test, is output, it is possible to provide an immunological test apparatus and an operation method thereof, an information processing apparatus and an operation method thereof, and an information processing system capable of effectively using the required determination time to prevent the spread of infection.

BRIEF DESCRIPTION OF THE DRAWINGS

FIG. 13 is a block diagram of an information processing server.

FIG. 14 is a diagram showing a first test record table.

FIG. 15 is a diagram showing a second test record table.

FIG. 16 is a diagram showing installation location information.

FIG. 17 is a diagram showing statistical information based on a first test record.

FIG. 18 is a diagram showing statistical information based on a second test record.

FIG. 28 is a diagram showing another example of the statistical information display screen.

DESCRIPTION OF THE PREFERRED EMBODIMENTS

Figure 1:
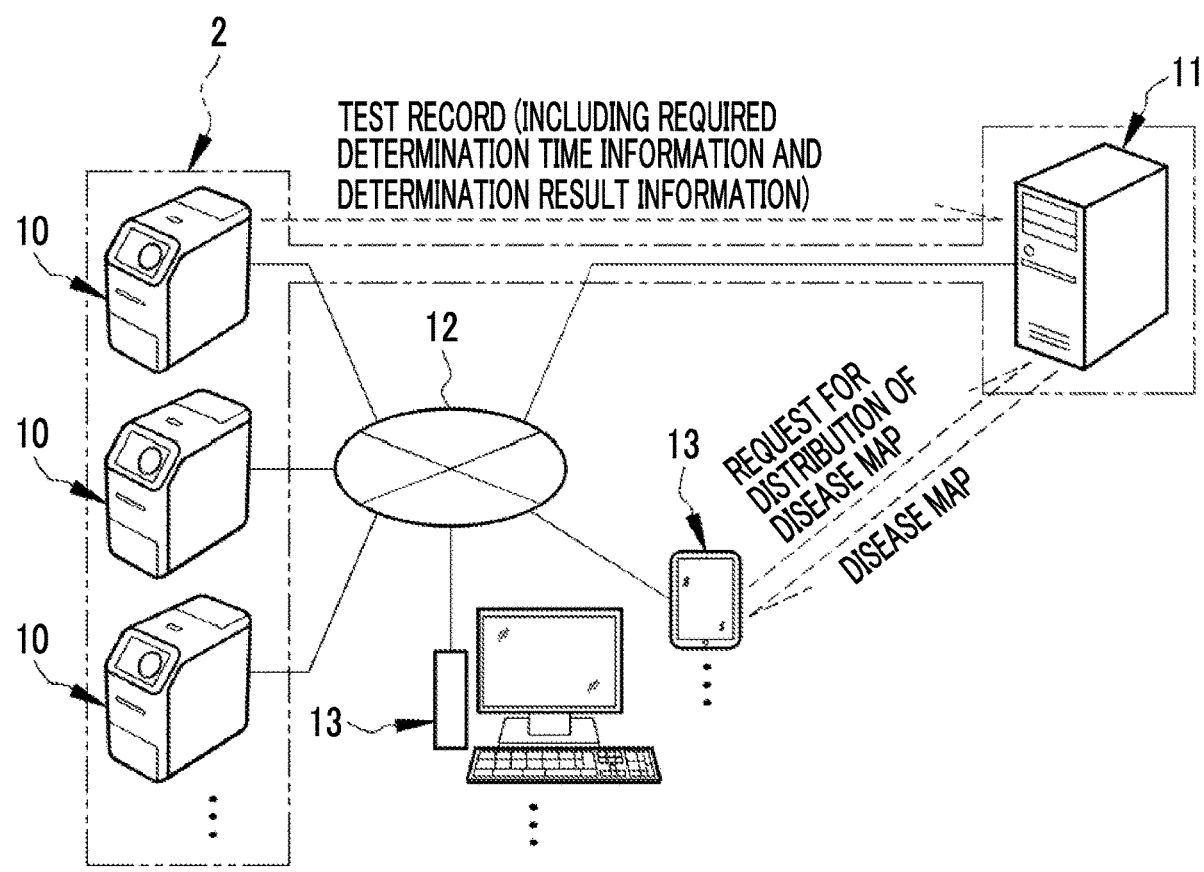
FIG. 1 is a diagram showing an information processing system.

In FIG. 1, an information processing system 2 comprises a plurality of immunological test apparatuses 10 and an information processing server 11 corresponding to an information processing apparatus. The immunological test apparatus 10 and the information processing server 11 are communicably connected to each other through a network 12, such as the Internet or a wide area network (WAN) called a public communication network. In the network 12, in consideration of information security, a virtual private network (VPN) is constructed, or a communication protocol with a high security level, such as hypertext transfer protocol security (HTTPS), is used.

The immunological test apparatus 10 is provided in a medical institution, such as a hospital, for example. The immunological test apparatus 10 performs an immunological test on a sample SSP (refer to FIG. 5). More specifically, the immunological test apparatus 10 determines whether or not A type influenza virus or B type influenza virus, which is a test substance, is present in the sample SSP. That is, the immunological test apparatus 10 performs a qualitative reaction test for testing positive and negative of influenza as an infectious disease. The sample SSP is, for example, a solution obtained by mixing body fluid, such as pharyngeal swab or nasal swab collected from a patient, with a predetermined extract.

The immunological test apparatus 10 transmits a test record 90 (refer to FIGS. 9 and 10) to the information processing server 11 through the network 12. The test record 90 includes determination result information 91. In addition to the determination result information 91, the test record 90 may include required determination time information 92 (refer to FIG. 10). The required determination time information 92 is information regarding the required determination time that is the elapsed time of the test taken until a determination result indicating that influenza virus is present in the sample SSP is obtained from the start of the test. The determination result information 91 is information indicating that influenza virus is present in the sample SSP literally, that is, information of A type influenza positive and/or B type influenza positive.

A plurality of client terminals 13 are connected to the network 12. Each of the client terminal 13 and the information processing server 11 is configured by installing a control program, such as an operating system, or various application programs (hereinafter, referred to as AP) on a computer as a base, such as a personal computer, a tablet computer, a server computer, or a workstation.

The information processing server 11 is managed by, for example, a sales company of the immunological test apparatus 10. The information processing server 11 receives the test record 90 transmitted from the immunological test apparatus 10 through the network 12. The sales company of the immunological test apparatus 10 has made a site for providing information based on the test record 90 on the Internet.

The client terminal 13 accesses the information providing site through the network 12 according to the operation instruction of the user, such as a medical staff member. The client terminal 13 transmits a request for distribution of a disease map 136 (refer to FIGS. 19 and FIG. 20), which is obtained by expressing the number of influenza patients for each area on a map, to the information processing server 11 through the information providing site. The information processing server 11 distributes the disease map 136 to the client terminal 13 of the distribution request source in response to the distribution request.

The information processing server 11 distributes the disease map 136 in the form of a screen (hereinafter, referred to as a disease map display screen 135; refer to FIGS. 19 and 20) that can be viewed on the web browser of the client terminal 13. Specifically, the information processing server 11 outputs the disease map display screen 135 in the form of screen data for web distribution that is created by a markup language, such as extensible markup language (XML), for example. Instead of the XML, other data description languages, such as JavaScript (registered trademark) Object Notation (JSON), may be used. In addition to the disease map display screen 135, the information processing server 11 distributes various screens, such as an authentication screen for access to the information providing site, to the client terminal 13 in the form of screen data for web distribution.

Figure 2:
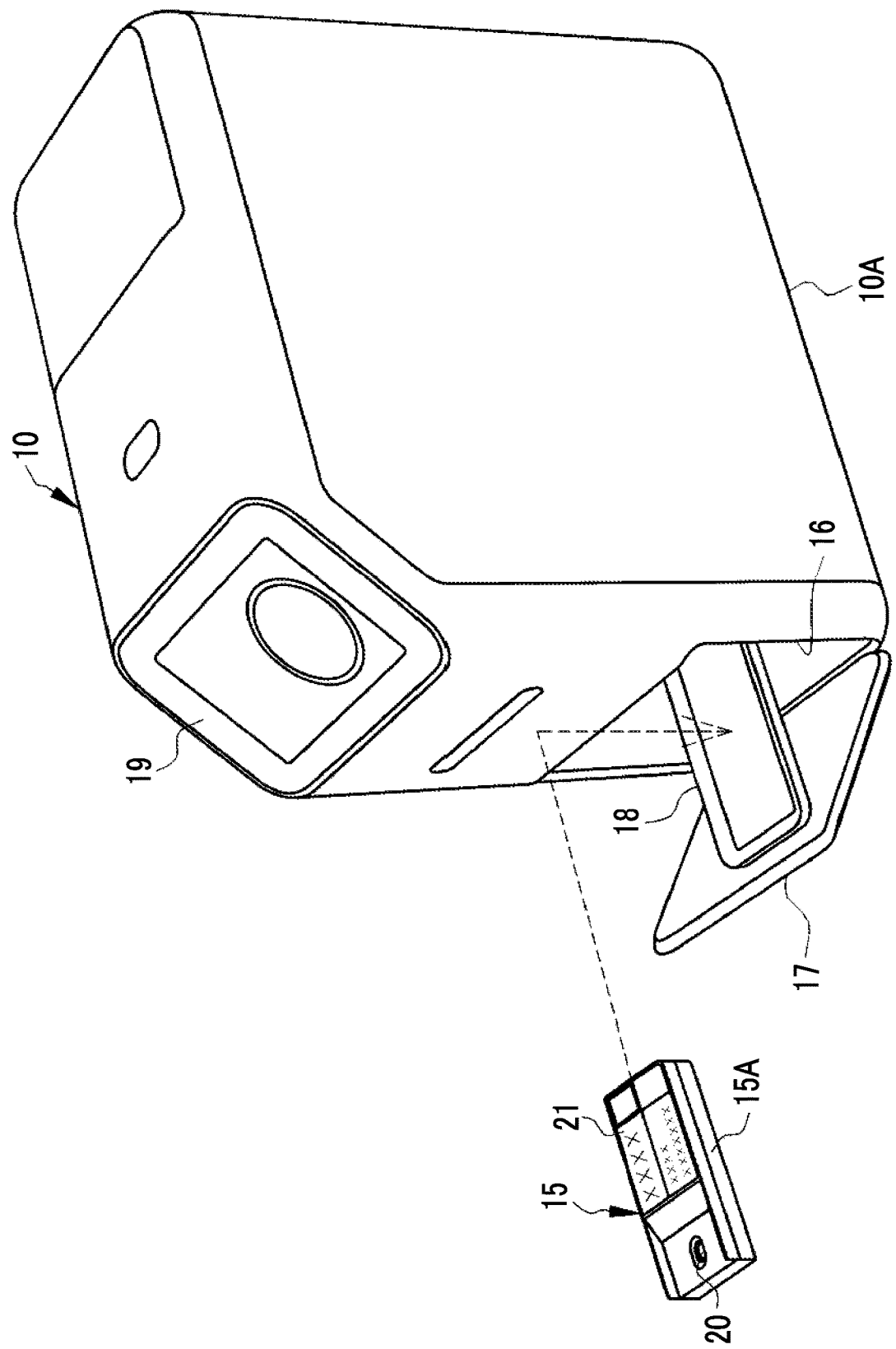
FIG. 2 is a perspective view showing the external appearance of an immunological test apparatus.

In FIG. 2, the immunological test apparatus 10 has an apparatus main body 10A. A rectangular opening 16 for receiving a dedicated cartridge 15 having the sample SSP dropped thereon, an openable lid 17 for covering the opening 16, and a tray-shaped cartridge loading unit 18 onto which the cartridge 15 is loaded are provided in the front lower portion of the apparatus main body 10A. The cartridge loading unit 18 slides in the opening and closing direction of the lid 17 in conjunction with the opening and closing of the lid 17. More specifically, the cartridge loading unit 18 slides between the exposed position shown in FIG. 2, which is mostly exposed from the opening 16 in a case where the lid 17 is opened, and the housing position shown in FIG. 3, which is housed in the apparatus main body 10A in a case where the lid 17 is closed.

The front upper portion of the apparatus main body 10A is an inclined surface portion, and a touch panel 19 is attached to the inclined surface portion. An operation instruction from the user is input to the touch panel 19, and information regarding the immunological test is displayed. Examples of the operation instruction include a test start instruction, a test stop instruction, and an instruction to print out a determination result indicating that influenza virus is present in the sample SSP. The information regarding the immunological test includes patient identification (ID) for identifying a patient from whom the sample SSP is collected, an elapsed time from the start of the test, a determination result, and the like.

The cartridge 15 has a case 15A in which a carrier 30 (refer to FIG. 3) is housed. On the upper surface of the case 15A, a reverse conical dropping port 20 through which the sample SSP is dropped is provided. In addition, a label 21 on which a patient ID and the like are written is attached to the upper surface of the case 15A.

Figure 3:
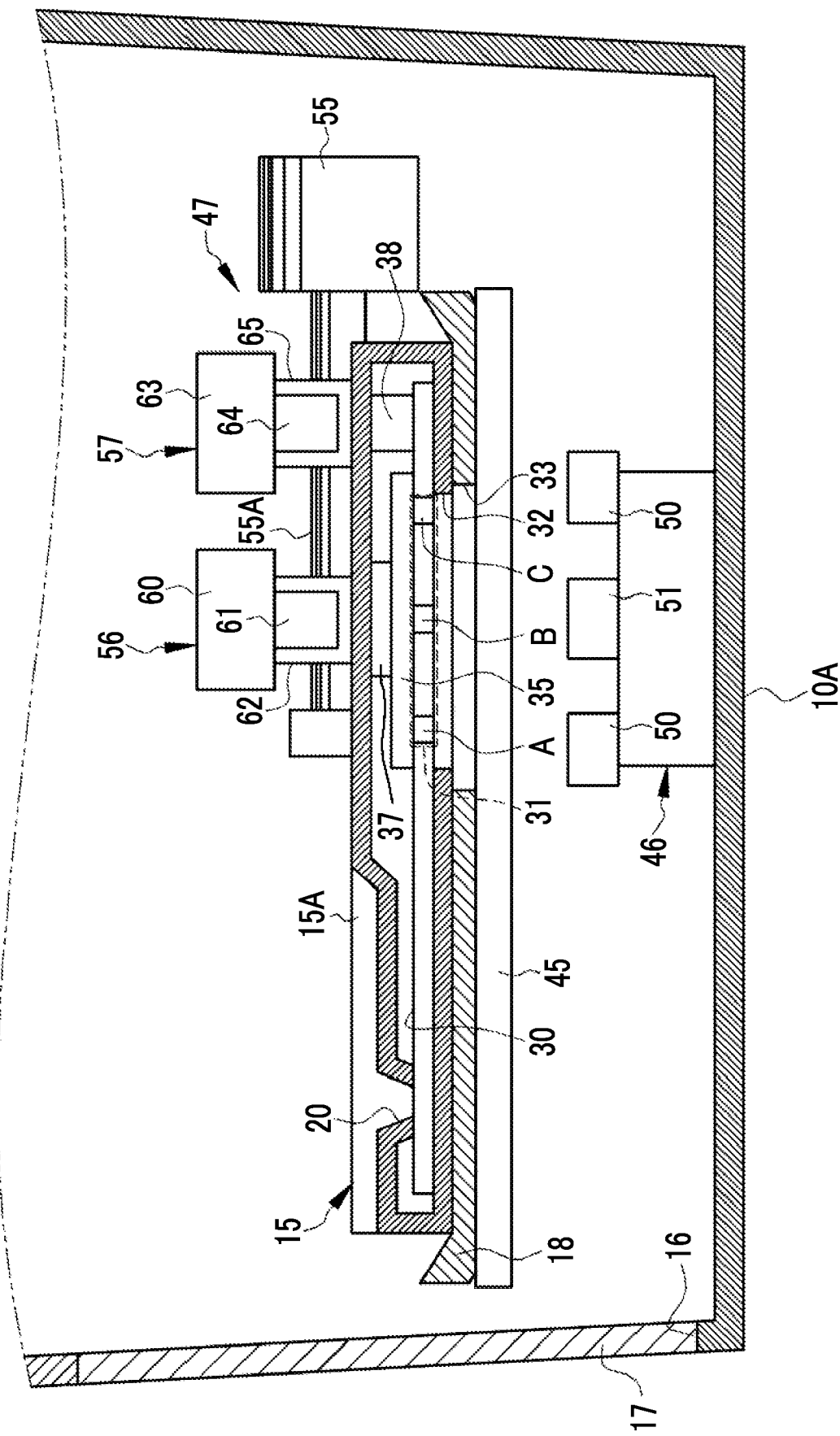
FIG. 3 is a partially broken side view of the immunological test apparatus.
Figure 4:
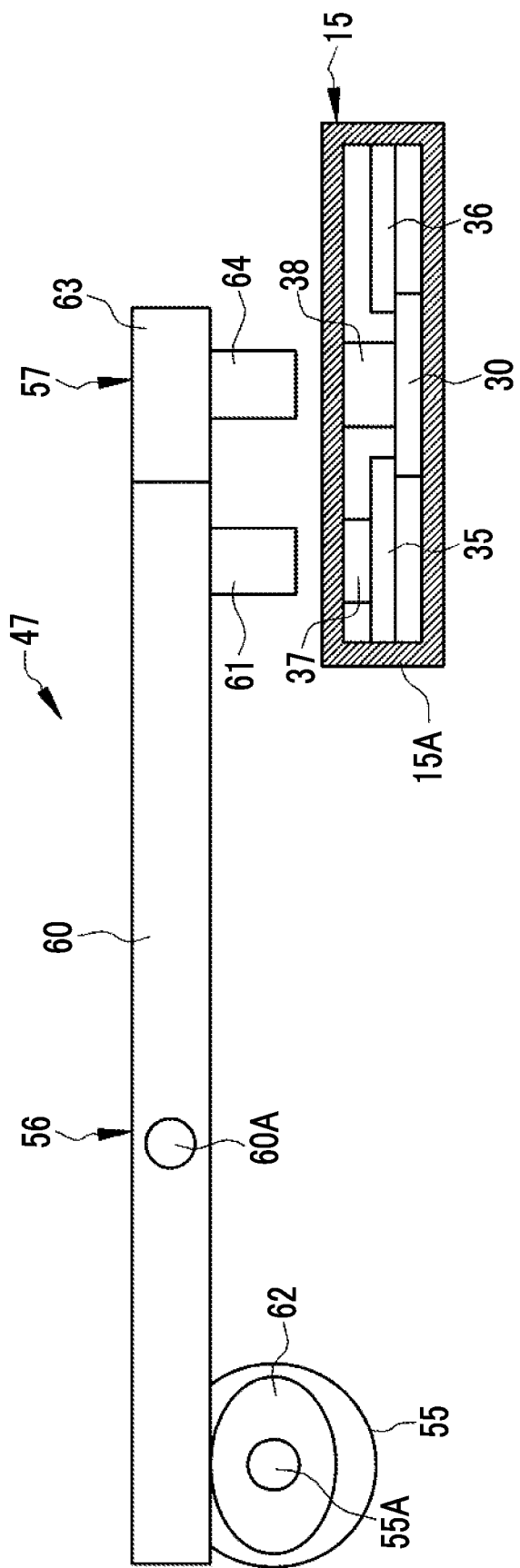
FIG. 4 is a diagram showing a chemical solution spreading unit and the inside of a cartridge.

As shown in the cutaway view of the cartridge 15 of FIGS. 3 and 4, a belt-shaped carrier 30 is housed in the case 15A along the longitudinal direction. The carrier 30 is, for example, a nitrocellulose film, and has a test region 31 formed by two test lines A and B and a control line C. On the test line A, a reagent that is combined with the A type influenza virus to be colored is fixed. On the test line B, a reagent that is combined with the B type influenza virus to be colored is fixed. The control line C is a line for determining whether or not the amount of sample SSP appropriate for measurement has normally flowed through the carrier 30, and makes a color in a case where the amount of sample SSP appropriate for measurement has normally flowed through the carrier 30.

The reagent of the test line A is anti-A type influenza virus antibody, anti-A type influenza virus antibody bonding gold colloid, anti-A type influenza virus antibody bonding colored latex, or the like. The reagent of the test line B is anti-B type influenza virus antibody, anti-B type influenza virus antibody bonding gold colloid, anti-B type influenza virus antibody bonding colored latex, or the like.

On the lower surface of the case 15A, an observation window 32 for observing the coloration state of the test lines A and B and the control line C is formed. A similar observation window 33 is also formed in the cartridge loading unit 18 at a position corresponding to the observation window 32 of the case 15A.

In addition to the carrier 30, a solution feeding pad 35, a solution absorbing pad 36 (not shown in FIG. 3, refer to FIG. 4), a reducing solution pot 37, and a sensitizing solution pot 38 are housed in the case 15A. The solution feeding pad 35 and the solution absorbing pad 36 are disposed at positions interposing the carrier 30 from both sides in the test region 31 (refer to FIG. 5 and the like). The reducing solution pot 37 is disposed above the solution feeding pad 35, and stores a reducing solution SR (refer to FIG. 6) corresponding to a chemical solution for sensitizing the coloration state of the reagent. The sensitizing solution pot 38 is disposed above the end portion of the carrier 30 on the label 21 side, and stores a sensitizing solution SSE (refer to FIG. 7) corresponding to a chemical solution.

The reducing solution SR is a solution of ammonium iron sulfate that is a divalent iron ion-containing compound. On the other hand, the sensitizing solution SSE is a solution of silver nitrate that is a silver ion-containing compound. As described above, there are two types of chemical solutions of a solution of a divalent iron ion-containing compound (reducing solution SR) and a solution of a silver ion-containing compound (sensitizing solution SSE). The silver ion-containing compound may be silver acetate, silver lactate, silver butyrate, silver thiosulfate, or the like.

In FIG. 3, a guide rail 45, a measurement unit 46, and a chemical solution spreading unit 47 are provided in the apparatus main body 10A. The guide rail 45 guides a slide between the exposed position and the housing position of the cartridge loading unit 18.

In a case where the cartridge 15 is located at the housing position, the measurement unit 46 is disposed at a position facing the observation window 32 of the case 15A and the observation window 33 of the cartridge loading unit 18. The measurement unit 46 includes a pair of light sources 50 for emitting light to the test region 31, which is formed by the test lines A and B and the control line C, through the observation windows 32 and 33 and an imaging element 51 for imaging the test region 31.

The light source 50 is, for example, a module in which a light emitting diode (LED) is built, and emits white light. The light source 50 may emit monochromatic light as long as the chromaticity before and after sensitization processing, which will be described later, can be distinguished. The light source 50 can also be configured by a plurality of modules that emit monochromatic light components having different wavelengths. The imaging element 51 is, for example, a line sensor in which a plurality of photodiodes are linearly arranged or an area sensor in which a plurality of photodiodes are arranged in a matrix, and outputs an imaging signal corresponding to the amount of light received by the photodiodes.

The chemical solution spreading unit 47 performs sensitization processing for spreading the reducing solution SR and the sensitizing solution SSE, which are chemical solutions for sensitizing the coloration state of the reagent, on the carrier 30. The chemical solution spreading unit 47 has a motor 55, a first pressing unit 56, and a second pressing unit 57. The motor 55 is shared by the pressing units 56 and 57.

In FIG. 4, the first pressing unit 56 has a first arm 60 rotatable around a shaft 60A like a seesaw, a first pressing piece 61 fixed to a lower portion of the distal end of the first arm 60, and a first cam 62 disposed on the lower side of the rear end of the first arm 60. The first cam 62 is connected to a driving shaft 55A rotated by the motor 55 so as to be able to be connected and disconnected through an electromagnetic clutch or the like (not shown), for example. In a case where the first cam 62 rotates, the rear end of the first arm 60 is pushed up, and the first pressing piece 61 at the distal end is lowered. Similarly, the second pressing unit 57 has a second arm 63, a second pressing piece 64, and a second cam 65 (refer to FIG. 3), and the second pressing piece 64 is lowered by the rotation of the second cam 65.

The first pressing piece 61 is disposed immediately above the reducing solution pot 37 in a case where the cartridge 15 is located at the housing position. In a case where the first pressing piece 61 is lowered, the reducing solution pot 37 is crushed from the outside of the case 15A by the first pressing piece 61, and the reducing solution SR is spread from the reducing solution pot 37. On the other hand, the second pressing piece 64 is disposed immediately above the sensitizing solution pot 38 in a case where the cartridge 15 is located at the housing position. In a case where the second pressing piece 64 is lowered, the sensitizing solution pot 38 is crushed from the outside of the case 15A by the second pressing piece 64, and the sensitizing solution SSE is spread from the sensitizing solution pot 38.

Although not shown, an information reading unit for reading the information written on the label 21, a printer for printing out the determination result on a predetermined sheet, and the like are provided in the apparatus main body 10A. Similarly to the measurement unit 46, the information reading unit is configured to include a light source that emits light to the label 21 and an imaging element that images the label 21. The information reading unit is disposed at a position facing the label 21 in a case where the cartridge 15 is located at the housing position.

Figure 5:
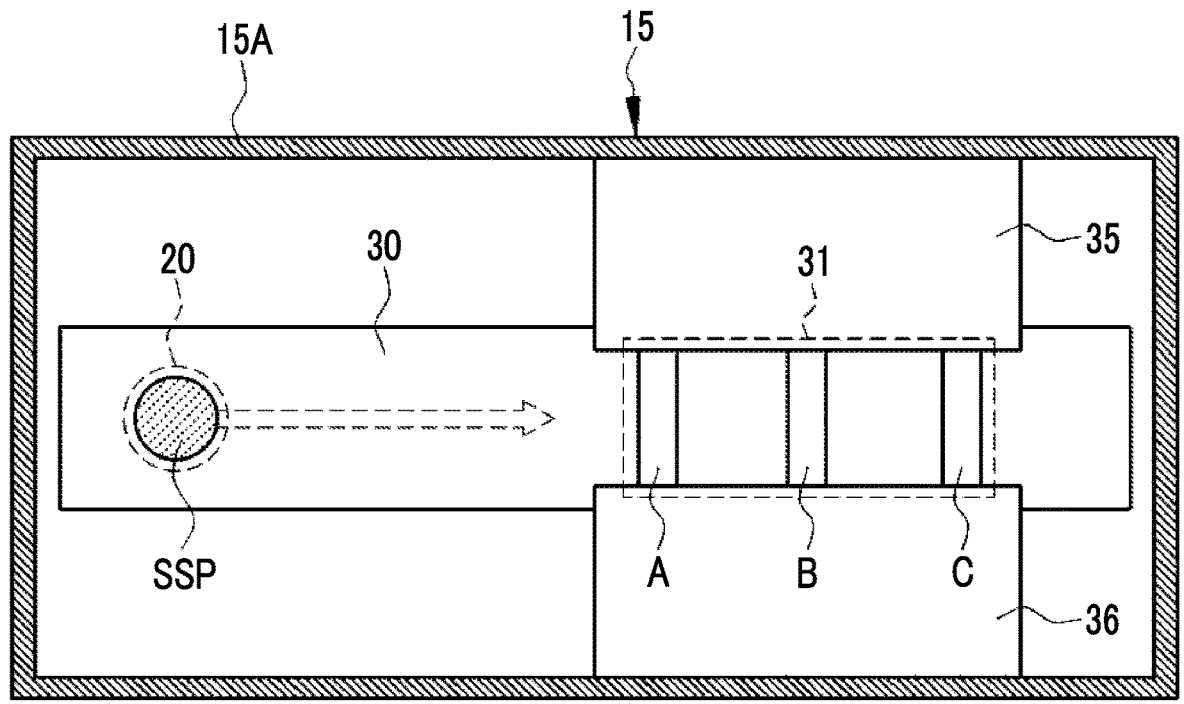
FIG. 5 is a diagram showing how a sample moves from a dropping port to a test region.

In FIG. 5, in the immunological test, first, the sample SSP is dropped onto the carrier 30 through the dropping port 20. The sample SSP moves from the dropping port 20 onto the carrier 30 toward the test region 31. The sample SSP reaches the test line A, then reaches the test line B, and finally reaches the control line C. Here, in a case where the A type influenza virus is present in the sample SSP, the reagent of the test line A is colored. In a case where the B type influenza virus is present in the sample SSP, the reagent of the test line B is colored.

The density of coloration of the reagent is correlated with the amount of influenza virus present in the sample SSP. That is, the density of coloration of the reagent is low in a case where only a small amount of influenza virus is present in the sample SSP, and the density of coloration of the reagent is high in a case where a large amount of influenza virus is present in the sample SSP. The amount of influenza virus in the early stage patient, who is a patient with relatively mild symptoms at the early stage of infection, is smaller than that in the middle stage patient, who is a patient with remarkable symptoms at the middle stage of infection. For this reason, the density of coloration of the reagent in the case of the early stage patient is lower than that in the case of the middle stage patient.

A region where a labeled substance is present is provided between the dropping port 20 of the carrier 30 and the test region 31. In the sample SSP, the labeled substance is mixed during movement from the dropping port 20 to the test region 31. The labeled substance is captured by the control line C, and accordingly the control line C is colored. Therefore, in a case where the sample SSP reaches the control line C after a predetermined time TE (for example, 15 minutes) has passed from dropping of the sample SSP, the control line C is colored regardless of the presence or absence of coloration of the reagent of the test lines A and B. In a case where the coloration of the control line C cannot be checked even after the time TE has passed, an error is determined.

Figure 6:
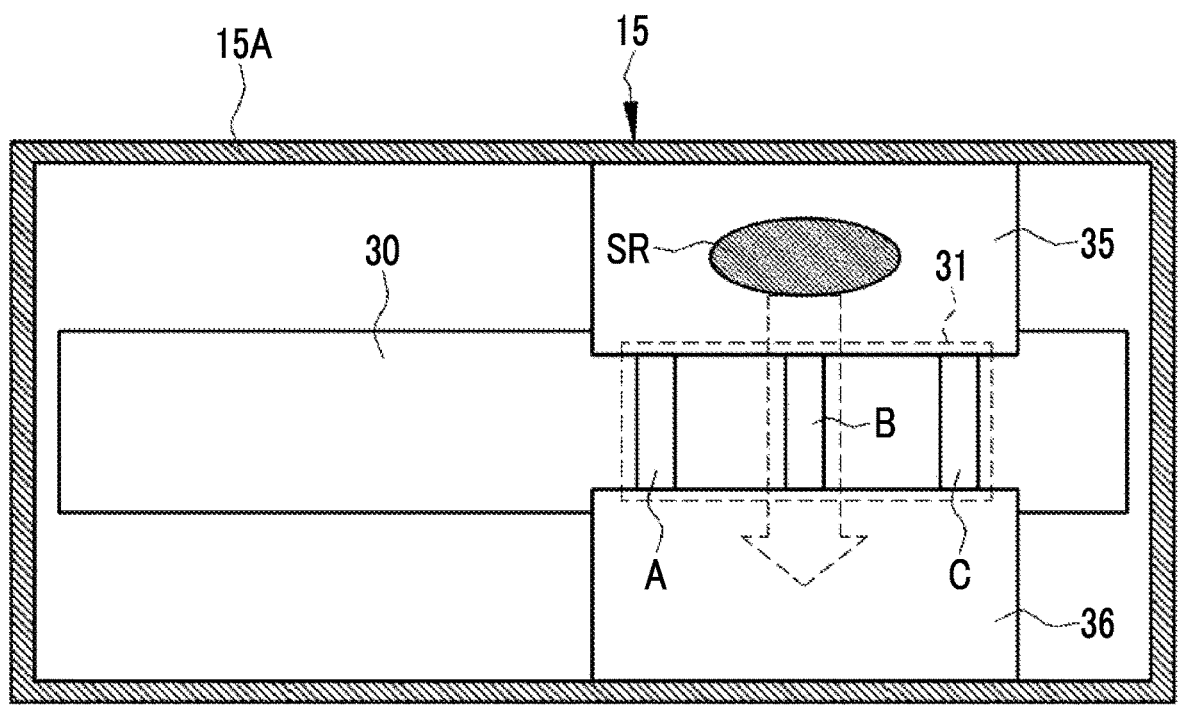
FIG. 6 is a diagram showing how a reducing solution is spread to the test region.

In FIG. 6, in a case where the first pressing unit 56 is driven and the reducing solution pot 37 is crushed by the first pressing piece 61, the reducing solution SR is dropped from the reducing solution pot 37 onto the solution feeding pad 35. The timing at which the reducing solution SR is dropped onto the solution feeding pad 35 is the timing of the start of the sensitization processing. The reducing solution SR is sent to the test region 31 along the short direction of the case 15A and absorbed by the solution absorbing pad 36.

Figure 7:
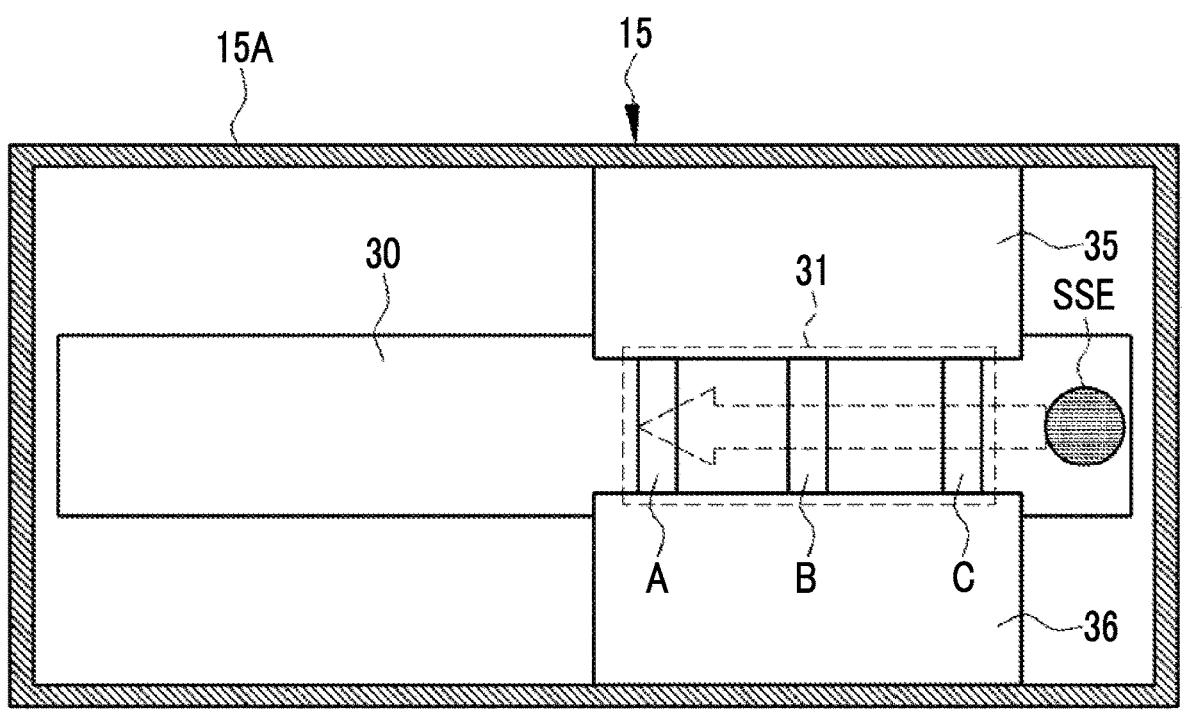
FIG. 7 is a diagram showing how a sensitizing solution is spread to the test region.

In FIG. 7, in a case where the second pressing unit 57 is driven and the sensitizing solution pot 38 is crushed by the second pressing piece 64, the sensitizing solution SSE is dropped from the sensitizing solution pot 38 onto the end portion of the carrier 30 on the label 21 side. The sensitizing solution SSE is sent to the test region 31 along the longitudinal direction of the case 15A.

Figure 8:
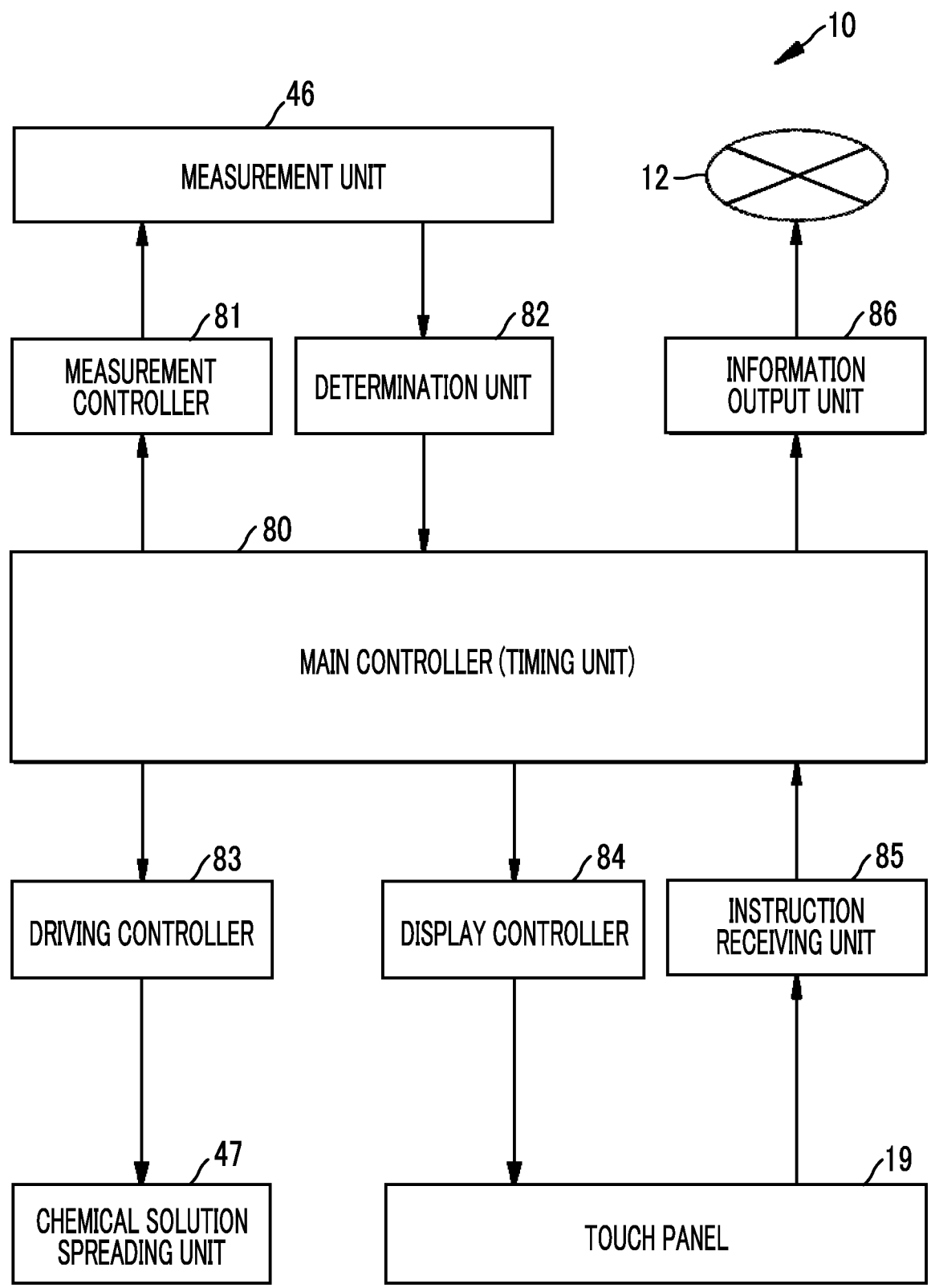
FIG. 8 is a block diagram of the immunological test apparatus.

In FIG. 8, a main controller 80 performs overall control of the immunological test apparatus 10. A measurement controller 81, a determination unit 82, a driving controller 83, a display controller 84, an instruction receiving unit 85, and an information output unit 86 are connected to the main controller 80.

The measurement controller 81 controls the driving of the measurement unit 46. More specifically, the measurement controller 81 drives the light source 50 and the imaging element 51 of the measurement unit 46 at predetermined time intervals (for example, one minute intervals), so that the light source 50 emits light to the test region 31 and the imaging element 51 images the test region 31.

The determination unit 82 receives an imaging signal from the imaging element 51 of the measurement unit 46 at predetermined intervals. The determination unit 82 determines whether or not A type influenza virus and/or B type influenza virus is present in the sample SSP from the coloration state (density, chromaticity) of the reagent derived based on the imaging signal. For example, in a case where the density and chromaticity of the coloration of the reagent exceed threshold values set in advance, the determination unit 82 determines that A type influenza virus and/or B type influenza virus is present in the sample SSP.

In a case where it is determined that A type influenza virus is present in the sample SSP, the determination unit 82 outputs a first determination result indicating that A type influenza virus is present in the sample SSP to the main controller 80. In a case where it is determined that B type influenza virus is present in the sample SSP, the determination unit 82 outputs a second determination result indicating that B type influenza virus is present in the sample SSP to the main controller 80. In addition, the determination unit 82 determines whether or not the measurement has ended correctly from the coloration state of the control line C, and outputs the determination result to the main controller 80.

The first determination result indicates that the patient, from whom the sample SSP has been collected, is infected with A type influenza virus (A type influenza positive). The second determination result indicates that the patient, from whom the sample SSP has been collected, is infected with B type influenza virus (B type influenza positive).

Assuming that the intensity of light emitted from the light source 50 to the test region 31 is I and the intensity of reflected light from the test region 31 imaged by the imaging element 51 is IR, the density OC of the coloration of the reagent is defined by the following Equation (1).

$$OC = \log_{10(IR/I)} \quad (1)$$

The chromaticity is a quantitative expression of the hue and the saturation of the color of the reagent, and is calculated from the imaging signal using a known calculation equation. As a color system of chromaticity, a general commission internationale de l'eclairage (CIE) color system can be used.

The driving controller 83 controls the driving of the chemical solution spreading unit 47. In practice, the driving controller 83 is a driver of the motor 55 of the chemical solution spreading unit 47. The driving controller 83 drives the chemical solution spreading unit 47 to start sensitization processing.

The main controller 80 corresponds to a timing unit, and counts an elapsed time TP from the start of the test. The main controller 80 outputs a driving command to the driving controller 83 in a case where at least one of the first determination result or the second determination result is not received from the determination unit 82 even though the elapsed time TP exceeds a set time TS (for example, 12 minutes) set in advance (TP>TS). The driving controller 83 drives the chemical solution spreading unit 47 in response to the driving command. That is, in a case where neither the first determination result nor the second determination result is obtained or either the first determination result or the second determination result is not obtained during a period from the start of the test to the set time TS (0<TP≤TS), the sensitization processing is started. Conversely, in a case where both the first determination result and the second determination result are obtained during the period from the start of the test to the set time TS, the sensitization processing is not performed.

In a case where the elapsed time TP becomes the time TE taken for the sample SSP to reach the control line C (TP=TE) and a determination result indicating that the measurement has ended correctly is received from the determination unit 82, the main controller 80 ends the test. In a case where neither the first determination result nor the second determination result is obtained at the end of the test, it is understood that the patient from whom the sample SSP has been collected is not infected with both A type influenza virus and B type influenza virus (A type influenza virus negative and B type influenza virus negative). In a case where the test has ended, the user can take out the cartridge 15 from the immunological test apparatus 10.

The display controller 84 controls the display of various display screens on the touch panel 19. The instruction receiving unit 85 receives the above-described various operation instructions input by the user through the touch panel 19.

In a case where a test start instruction is received by the instruction receiving unit 85, the main controller 80 starts counting the elapsed time TP, and the measurement controller 81 causes the measurement unit 46 to start measurement. In a case where a test stop instruction is received by the instruction receiving unit 85, the main controller 80 stops the test. Therefore, the user can take out the cartridge 15 from the immunological test apparatus 10 as in the case where the test ends. In a case where an instruction to print out the determination result is received by the instruction receiving unit 85, the printer prints out the determination result on a predetermined sheet.

The test stop instruction can be input in a case where a determination result indicating that at least one of A type influenza virus or B type influenza virus is present in the sample SSP is obtained. Therefore, for this reason, in a case where the first determination result indicating that A type influenza virus is present in the sample SSP is obtained, the test can be stopped immediately without waiting for the second determination result indicating that B type influenza virus is present in the sample SSP.

In the qualitative reaction test of influenza, it does not matter so much whether the patient is infected with either A type influenza virus or B type influenza virus. This is because, regardless of A type influenza virus or B type influenza virus, treatment methods such as the type, dose, and usage of the drug to be administered are generally common. For this reason, in a case where the infection with either A type influenza virus or B type influenza virus is found, the minimum purpose of the qualitative reaction test of influenza can be achieved.

Therefore, in a case where a determination result indicating that at least one of A type influenza virus or B type influenza virus is present in the sample SSP is obtained, a test stop instruction is received, and accordingly the stopping of the test does not cause any problem. For this reason, in this example, in a case where a determination result indicating that at least one of A type influenza virus or B type influenza virus is present in the sample SSP is obtained, it is possible to stop the test.

The information output unit 86 outputs required determination time information regarding the required determination time, which is the elapsed time taken until the determination result indicating that influenza virus is present in the sample SSP is obtained, so as to be associated with information of the determination result. More specifically, the information output unit 86 transmits the required determination time information and the information of the determination result to the information processing server 11, which is connected through the network 12, for each test.

Here, the sensitization processing is performed only in a case where the density of coloration of the reagent is low as it is and confirmation that influenza virus is present in the sample SSP cannot be obtained, and is not performed in a case where the density of coloration of the reagent is sufficiently high. For this reason, it is considered that the sensitization processing is performed in the case of an early stage patient having only a small amount of influenza virus in the sample SSP and is not performed in the case of a middle stage patient having a large amount of influenza virus in the sample SSP.

Before the sensitization processing is performed, at least a time from the start of the test to the set time TS is required. Therefore, in order to distinguish whether the patient from whom the sample SSP has been collected is an early stage patient or a middle stage patient based on the required determination time information, the required determination time information may be at least information indicating that the elapsed time TP exceeds the set time TS and further may be information indicating that the sensitization processing has been performed. In a case where information indicating that the sensitization processing has been performed is output as the required determination time information, a distinction between the early stage patient and the middle stage patient is made according to the presence and absence of the information. Therefore, in a case where the sensitization processing is not performed, it is not necessary to output the required determination time information.

Figure 9:
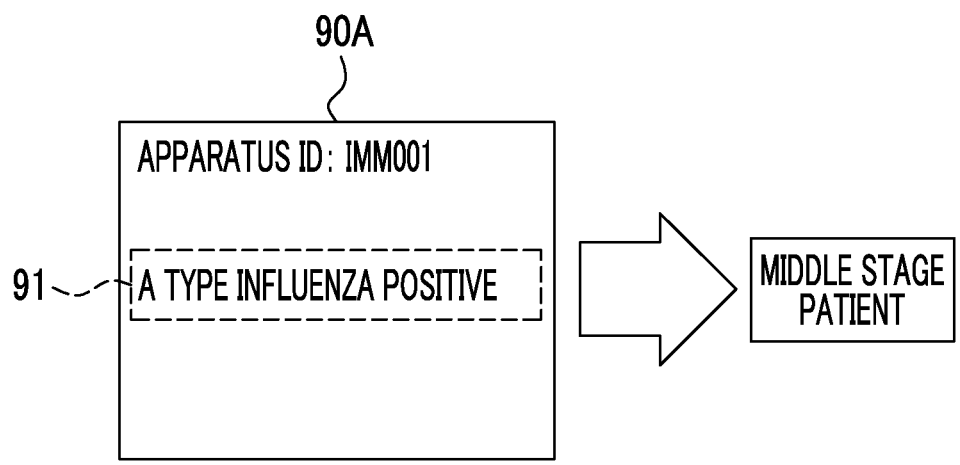
FIG. 9 is a diagram showing a first test record.
Figure 10:
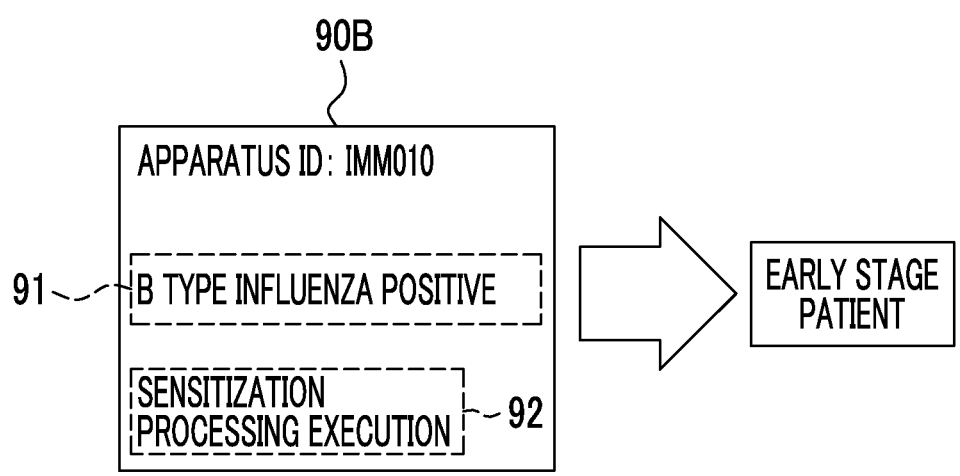
FIG. 10 is a diagram showing a second test record.

Therefore, the information output unit 86 outputs a first test record 90A shown in FIG. 9 in a case where the sensitization processing is not performed, and outputs a second test record 90B shown in FIG. 10 in a case where the sensitization processing is performed. The first test record 90A shown in FIG. 9 that is output in a case where the sensitization processing is not performed is obtained by attaching an apparatus ID for identifying the immunological test apparatus 10 to the determination result information 91. On the other hand, the second test record 90B shown in FIG. 10 that is output in a case where the sensitization processing is performed has the required determination time information 92 in addition to the determination result information 91, and is obtained by adding an apparatus ID to these.

In FIG. 9, "A type influenza positive" indicating the first determination result is exemplified as the determination result information 91. In FIG. 10, "B type influenza positive" indicating the second determination result is exemplified as the determination result information 91. The required determination time information 92 is "perform sensitization processing", and is information indicating that the sensitization processing has been performed.

Thus, the information output unit 86 outputs, as the required determination time information 92, information indicating that at least the elapsed time TP exceeds the set time TS, that is, information indicating that the sensitization processing has been performed. In addition, the information output unit 86 outputs the required determination time information 92 only in a case where the sensitization processing is performed.

Figure 11:
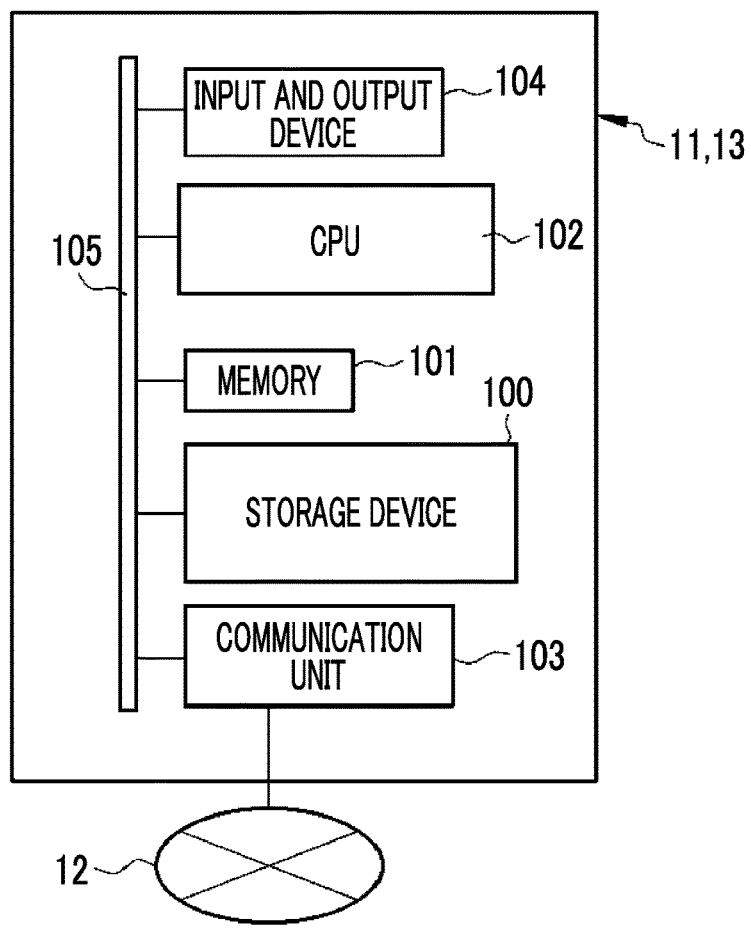
FIG. 11 is a block diagram of a computer that forms an information processing server and a client terminal.

In FIG. 11, the basic configurations of computers that form the information processing server 11 and the client terminal 13 are the same, and each computer comprises a storage device 100, a memory 101, a central processing unit (CPU) 102, a communication unit 103, and an input and output device 104. These are connected to each other through a data bus 105.

The storage device 100 is a hard disk drive, which is built into a computer that forms the information processing server 11 or the like or which is connected to the computer through a cable or a network, or a disk array formed by connecting a plurality of hard disk drives. A control program such as an operating system, various application programs, various kinds of data associated with these programs, and the like are stored in the storage device 100.

The memory 101 is a work memory for the CPU 102 to execute processing. The CPU 102 performs overall control of each unit of the computer by loading a program stored in the storage device 100 to the memory 101 and executing the processing according to the program. The communication unit 103 is a network interface to perform transmission control of various kinds of information through the network 12. The input and output device 104 is a display unit, such as a display, and an operation unit, such as a keyboard or a mouse, or a touch panel (serving as both a display unit and an operation unit).

In the following description, for the sake of distinction, a suffix "S" is attached to the reference numeral of each unit of the computer that forms the information processing server 11, and a suffix "L" is attached to the reference numeral of each unit of the computer that forms the client terminal 13.

Figure 12:
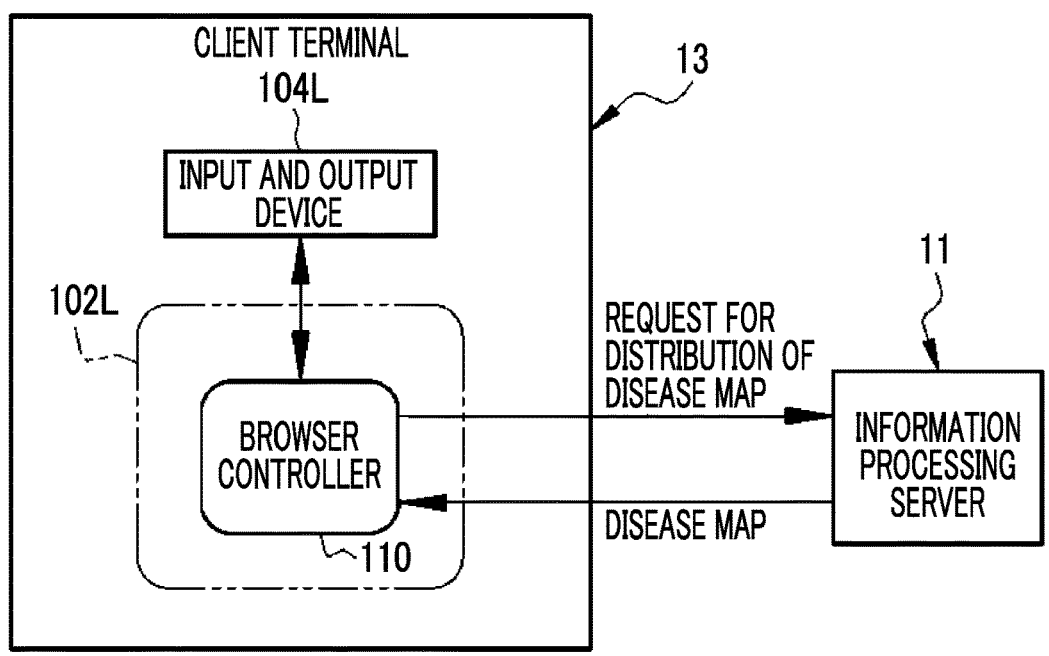
FIG. 12 is a block diagram of a client terminal.

In FIG. 12, in a case where the web browser is started, the CPU 102L of the client terminal 13 cooperates with the memory 101 or the like to function as a browser controller 110. The browser controller 110 controls the operation of the web browser. The browser controller 110 receives screen data of various screens from the information processing server 11. The browser controller 110 reproduces various screens to be displayed on the web browser based on the screen data, and displays the various screens on the display unit of the input and output device 104L.

The browser controller 110 receives various operation instructions input by the user through various screens. Examples of the operation instruction include an instruction for access to the information providing site, an instruction to distribute the disease map 136, and the like. The browser controller 110 issues various requests according to the operation instructions to the information processing server 11.

The access instruction includes user ID and password input by the user on the access authentication screen. In a case where there is an access instruction, the browser controller 110 issues an access request, which includes an address for identifying each client terminal 13 and a user ID and a password, to the information processing server 11. In a case where there is an instruction to distribute the disease map 136, the browser controller 110 issues a request for distribution of the disease map 136 including the address of the client terminal 13 to the information processing server 11.

In FIG. 13, an operation program 115 as an AP is stored in the storage device 100S of the information processing server 11. The operation program 115 is an AP for making the computer that forms the information processing server 11 function as an information processing apparatus. In addition to the operation program 115, a test record table 116 and an installation location information 117 are stored in the storage device 100S.

In a case where the operation program 115 is started, the CPU 102S of the information processing server 11 cooperates with the memory 101 or the like to function as a reception unit 120, an information management unit 121, a request receiving unit 122, a statistical information creation unit 123, a map creation unit 124, and a screen output controller 125.

The reception unit 120 has a reception function for receiving the test record 90 transmitted from the immunological test apparatus 10 through the network 12. In the case of the first test record 90A, the reception unit 120 receives only the determination result information 91. In the case of the second test record 90B, the reception unit 120 receives the required determination time information 92 in addition to the determination result information 91. The reception unit 120 outputs the received test record 90 to the information management unit 121.

The information management unit 121 manages storage of various kinds of information in the storage device 100S and reading of various kinds of information from the storage device 100S. Specifically, the information management unit 121 stores the test record 90 from the reception unit 120 in the test record table 116. The information management unit 121 transmits the test record 90 stored in the test record table 116 and the installation location information 117 to the statistical information creation unit 123. The test record 90 stored in the test record table 116 for more than a predetermined period (for example, one year) may be deleted from the test record table 116.

The request receiving unit 122 receives various requests from the client terminal 13 including the request for distribution of the disease map 136. The request receiving unit 122 outputs the request for distribution of the disease map 136 to the statistical information creation unit 123.

The statistical information creation unit 123 has a statistical information creation function for receiving a request for distribution of the disease map 136 from the request receiving unit 122 and creating statistical information 130 (refer to FIGS. 17 and 18) based on the installation location information 117 and the test record 90 from the information management unit 121. The statistical information creation unit 123 outputs the created statistical information 130 to the map creation unit 124.

The map creation unit 124 creates the disease map 136 by expressing the number of influenza patients for each area on a map based on the statistical information 130 from the statistical information creation unit 123. The map creation unit 124 outputs the created disease map 136 to the screen output controller 125.

The screen output controller 125 corresponds to an output controller that performs output control of the disease map 136. The screen output controller 125 controls distribution of various screens including the disease map display screen 135 to the client terminal 13. More specifically, the screen output controller 125 generates screen data of various screens for web distribution, and distributes the screen data to the client terminal 13 of the distribution request source.

The test record table 116 has two types of tables, a first test record table 116A shown in FIG. 14 in which the first test record 90A is stored and a second test record table 116B shown in FIG. 15 in which the second test record 90B is stored. The first test record 90A and the second test record 90B are stored in the tables 116A and 116B, respectively, together with the date and time received by the reception unit 120.

The first test record table 116A is a collection of first test records 90A that are output in a case where the sensitization processing is not performed. Therefore, since there is no need for sensitization processing, this can be said to be accumulated information of a middle stage patient having influenza virus in the sample SSP. On the other hand, the second test record table 116B is a collection of second test records 90B that are output in a case where the sensitization processing is performed. Therefore, since there is only a very small amount of influenza virus in the sample SSP, this can be said to be accumulated information of an early stage patient for whom the sensitization processing is required.

In FIG. 16, in the installation location information 117, the address (prefecture, municipality, aza, and the like) of the medical institution where the immunological test apparatus 10 is installed is registered as the installation location for each apparatus ID of the immunological test apparatus 10. According to the installation location information 117, the area where each immunological test apparatus 10 is installed, and therefore, the area of the transmission source of the test record 90, becomes clear on a prefectural basis, a municipality basis, or an aza basis. The address is input by the administrator of the information processing server 11 through the input and output device 104 in a case where the immunological test apparatus 10 is delivered to the medical institution, for example. Alternatively, the user may be made to input the address at the information providing site in the form of online user registration at the time of purchase of the immunological test apparatus 10.

In a case where a request for distribution of the disease map 136 is received from the request receiving unit 122, the statistical information creation unit 123 outputs an extraction command to the information management unit 121. In response to the extraction command, the information management unit 121 extracts the test record 90 whose reception date and time is within a predetermined period (for example, one week before the date on which the request for distribution of the disease map 136 is received) from the test record table 116. The information management unit 121 outputs the extracted test record 90 to the statistical information creation unit 123.

The statistical information creation unit 123 determines from which area each test record 90 from the information management unit 121 has been transmitted by comparing the apparatus ID of the test record 90 with the apparatus ID of the installation location information 117. For example, in the case of the first test record 90A having an apparatus ID "IMM001" in FIG. 14, since the address of the apparatus ID "IMM001" is "Kitadaika, Toshima-ku, Tokyo . . . " according to the installation location information 117, it is determined that the area of the transmission source is "Kitadaika, Toshima-ku, Tokyo . . . ". In addition, for example, in the case of the second test record 90B having an apparatus ID "IMM100" in FIG. 15, since the address of the apparatus ID "IMM100" is "Kawagoe City, Saitama Prefecture . . . " according to the installation location information 117, it is determined that the area of the transmission source is "Kawagoe City, Saitama Prefecture . . . ". The statistical information creation unit 123 summarizes the determination result of the area of the transmission source of each test record 90, which is obtained as described above, as the statistical information 130.

The statistical information 130A shown in FIG. 17 is the result of counting the number of first test records 90A for each prefecture of the transmission source of the first test record 90A that is determined by comparing the apparatus ID of the first test record 90A with the apparatus ID of the installation location information 117. The number of first test records 90A for each prefecture indicates the number of middle stage influenza patients for each prefecture.

The statistical information 130B shown in FIG. 18 is the result of counting the number of second test records 90B for each prefecture of the transmission source of the second test record 90B that is determined by comparing the apparatus ID of the second test record 90B with the apparatus ID of the installation location information 117. The number of second test records 90B for each prefecture indicates the number of early stage influenza patients for each prefecture whereas the number of first test records 90A for each procedure in the statistical information 130A in FIG. 17 indicates the number of middle stage influenza patients for each prefecture.

In the statistical information 130A and the statistical information 130B, since the test records 90 (patients) to be counted are different, the numbers are not necessarily the same even in the same prefecture. There is a prefecture (such as Saitama Prefecture) in which the number of first test records 90A (the number of middle stage patients) is larger than the number of second test records 90B (the number of early stage patients), and conversely, there is a prefecture (such as Chiba Prefecture) in which the number of second test records 90B (the number of early stage patients) is larger than the number of first test records 90A (the number of middle stage patients). In addition, there is a prefecture (such as Kanagawa Prefecture) in which the number of first test records 90A (the number of middle stage patients) and the number of second test records 90B (the number of early stage patients) are approximately the same.

In addition to the statistical information 130A indicating the number of middle stage influenza patients for each prefecture shown in FIG. 17 and the statistical information 130B indicating the number of early stage influenza patients for each prefecture shown in FIG. 18, the statistical information creation unit 123 can also create, as statistical information, the total number of influenza patients (the number of middle stage patients+ the number of early stage patients) for each prefecture, the number of middle stage patients or the number of early stage patients for each of A type influenza and B type influenza for each prefecture, and the number of middle stage patients, the number of early stage patients, and the total number of patients for each municipality instead of each prefecture.

Figure 19:
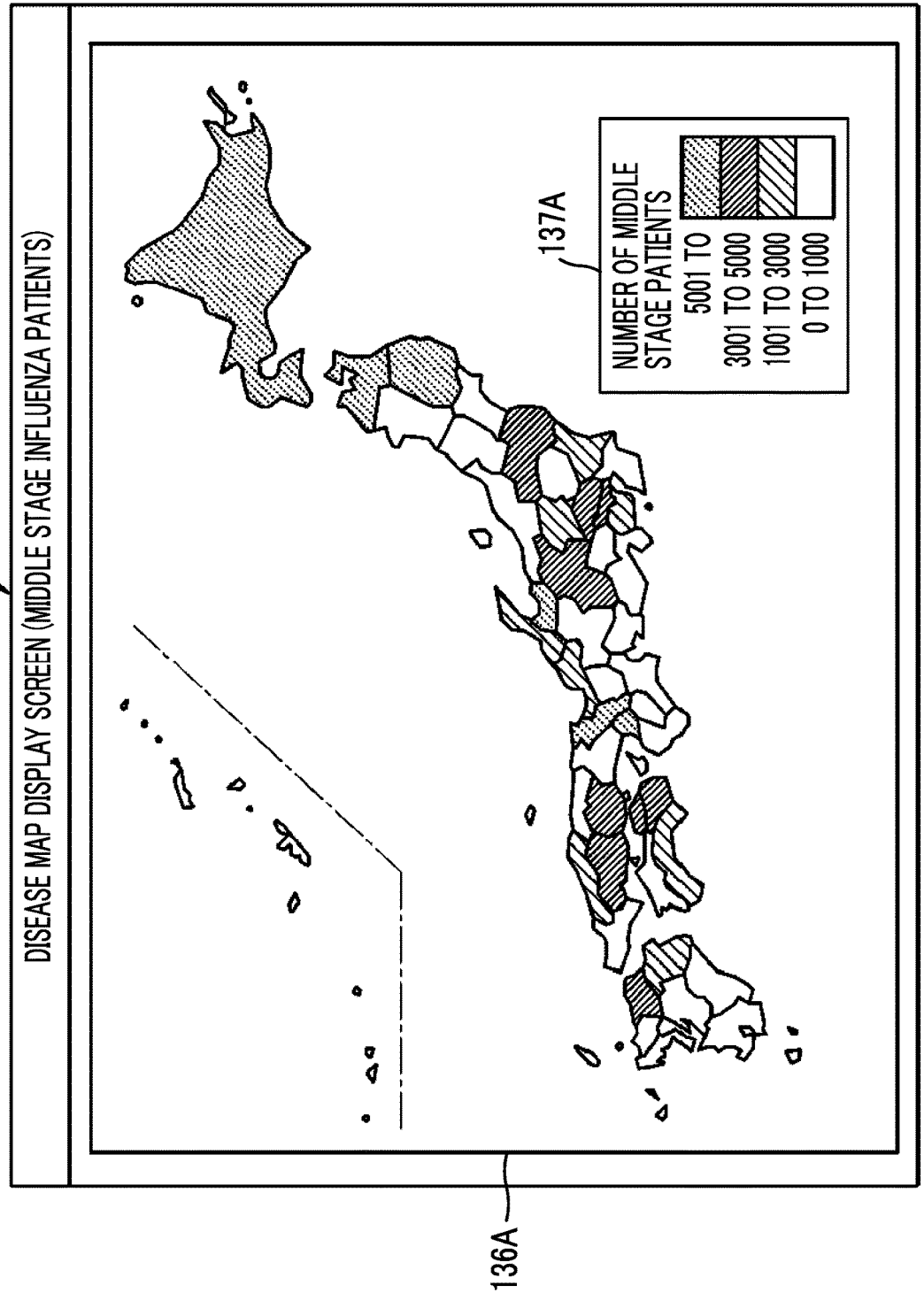
FIG. 19 is a diagram showing a disease map display screen on which a disease map of middle stage patients is displayed.
Figure 20:
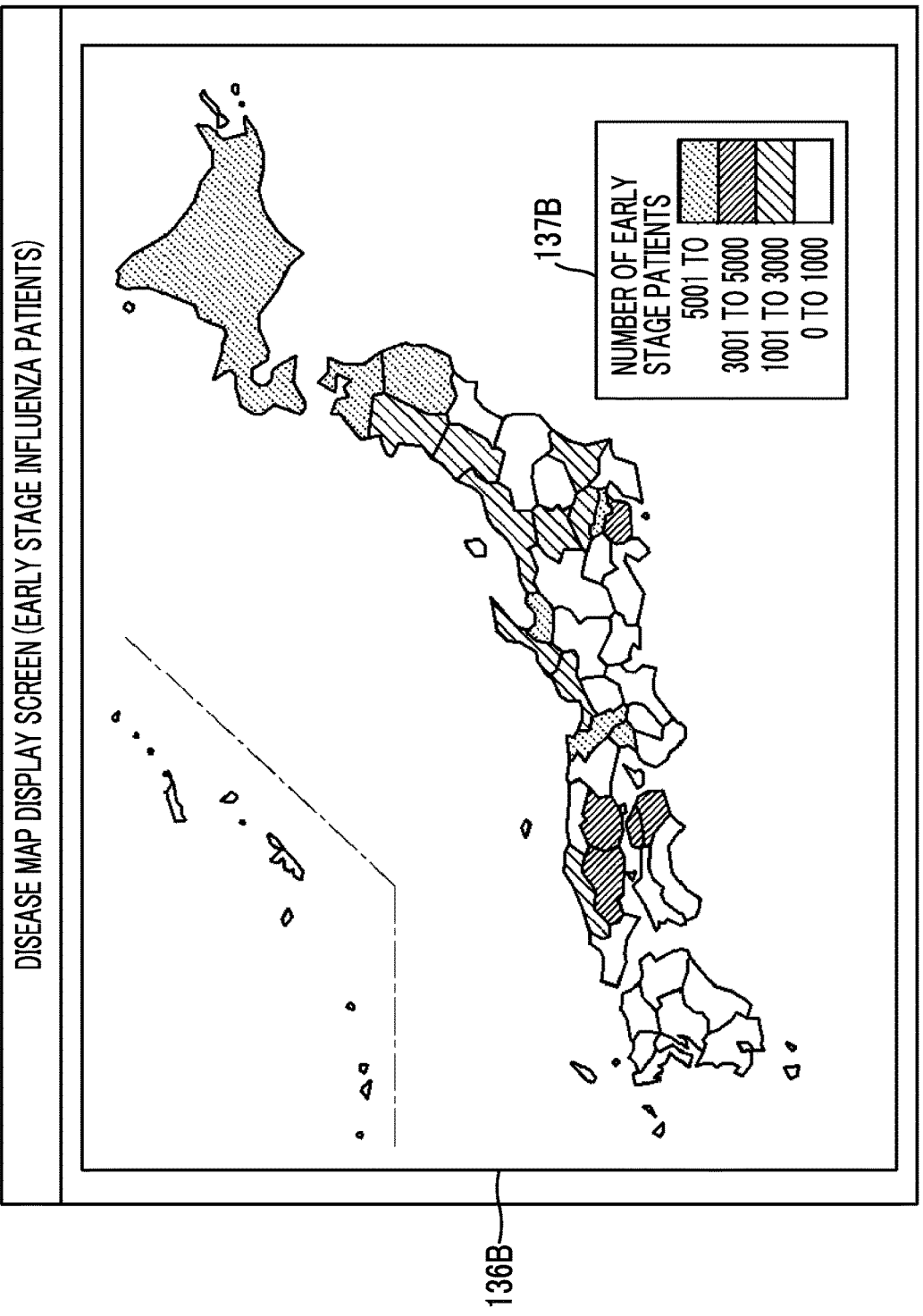
FIG. 20 is a diagram showing a disease map display screen on which a disease map of early stage patients is displayed.

In FIGS. 19 and 20, the disease map 136 and a legend 137 created by the map creation unit 124 based on the statistical information 130 from the statistical information creation unit 123 are displayed on the disease map display screen 135. The disease map 136 shown in FIGS. 19 and 20 is based on a Japanese map in which all prefectures are separated from each other. In the disease map 136, sections of the respective prefectures are filled with colors and/or patterns shown in the legend 137 according to the number of patients in the statistical information 130.

FIG. 19 exemplifies the disease map 136A of middle stage patients created based on the statistical information 130A shown in FIG. 17 and the legend 137A. On the other hand, FIG. 20 exemplifies the disease map 136B of early stage patients created based on the statistical information 130B shown in FIG. 18 and the legend 137B.

Figure 21:
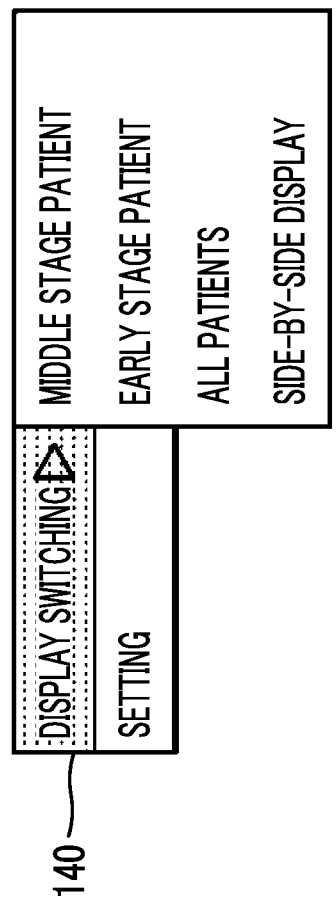
FIG. 21 is a diagram showing a menu used for display switching of a disease map.

Display switching between the disease map 136A shown in FIG. 19 and the disease map 136B shown in FIG. 20 is performed using a menu 140 shown in FIG. 21, for example. The menu 140 is displayed on the disease map display screen 135 by right-clicking the mouse of the client terminal 13, for example. "Display switching" options of the menu 140 include "all patients" in which the disease map 136 (not shown) of all patients is displayed and "side-by-side display" in which the disease map 136A and the disease map 136B are displayed side by side (not shown) in addition to "middle stage patients" in which the disease map 136A of middle stage patients is displayed and "early stage patients" in which the disease map 136B of early stage patients is displayed. In a case where "setting" of the menu 140 is selected, setting of the legend 137, setting of the type of influenza targeted in the statistical information 130, and the like can be performed.

In addition to the map of the whole Japan shown in FIGS. 19 and 20, a map of each prefecture in which municipalities are divided is also prepared as a base map of the disease map 136. In a case where one of the prefectures is selected in the display state shown in FIGS. 19 and 20, the disease map 136 (not shown) based on a map in which the municipalities of the selected prefecture are divided is displayed instead of the disease map 136 based on the map of the whole Japan shown in FIGS. 19 and 20. In this case, the sections of the respective municipalities are filled based on the legend and the statistical information indicating the number of middle stage patients, the number of early stage patients, and the total number of patients for each municipality.

Hereinafter, the operation based on the above configuration will be described with reference to the flowchart shown in FIGS. 22 to 25. First, the user applies the sample SSP, which is collected from a patient to be subjected to an immunological test, onto the dropping port 20 of the cartridge 15, opens the lid 17 to load the cartridge 15 into the cartridge loading unit 18, and closes the lid 17. Then, the user operates the touch panel 19 to input a test start instruction. Then, the test start instruction is received by the instruction receiving unit 85.

Figure 22:
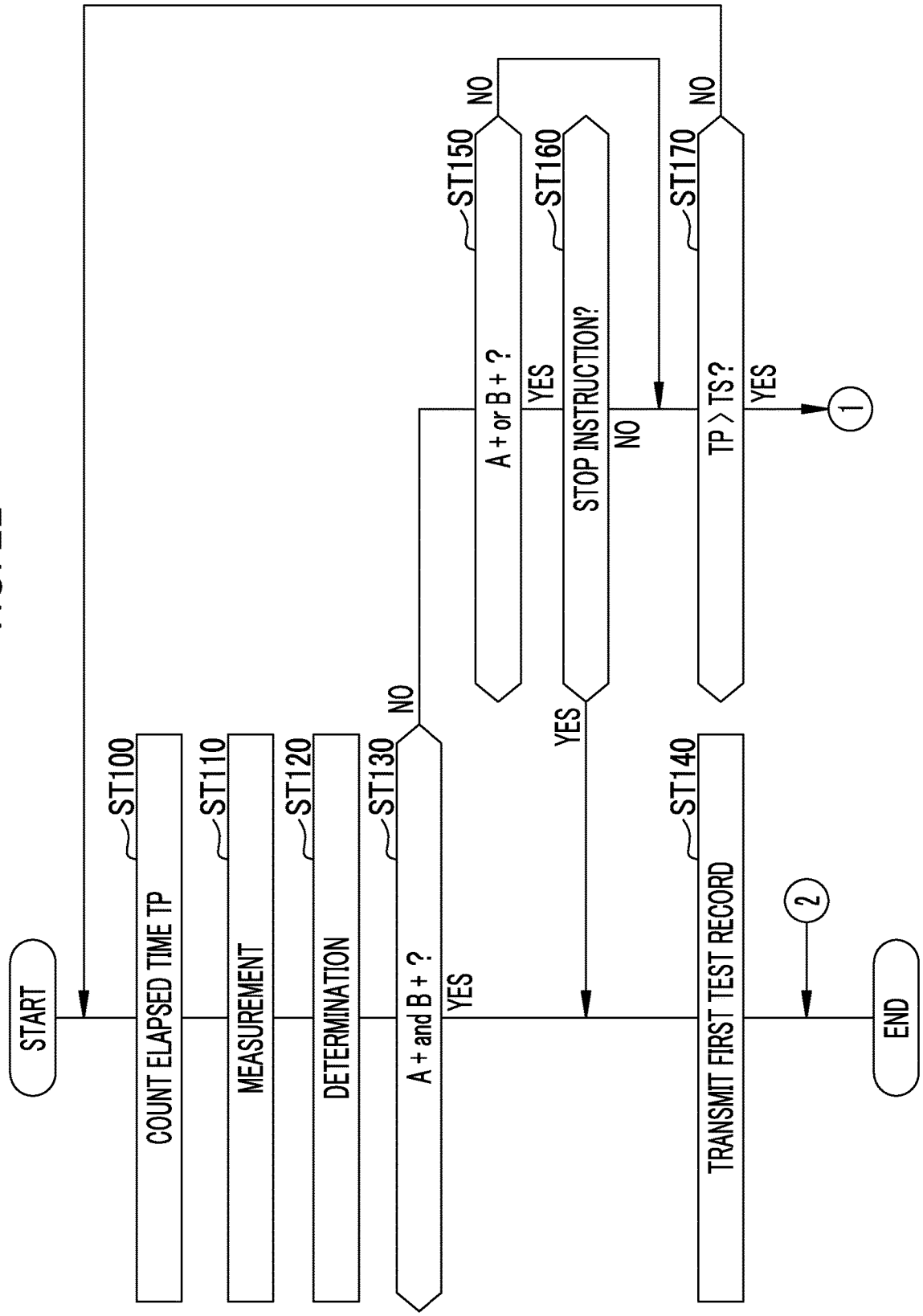
FIG. 22 is a flowchart showing the procedure of processing of the immunological test apparatus.

In a case where the test start instruction is received by the instruction receiving unit 85, counting of the elapsed time TP is started by the main controller 80 (step ST100 in FIG. 22, timing step). Then, measurement is started by the measurement unit 46 (step ST110). Then, an imaging signal is output from the imaging element 51 of the measurement unit 46 to the determination unit 82. Then, the determination unit 82 derives the coloration state (density, chromaticity) of the reagent based on the imaging signal, and determines whether or not influenza virus is present in the sample SSP from the coloration state (density, chromaticity) of the reagent (step ST120).

In a case where both the first determination result indicating that A type influenza virus is present in the sample SSP and the second determination result indicating that B type influenza virus is present in the sample SSP are obtained in the determination of step ST120 (YES in step ST130), the first test record 90A is transmitted from the information output unit 86 to the information processing server 11 (step ST140). In this case, the main controller 80 ends the test without waiting for the elapsed time TP to become the time TE. The user can take out the cartridge 15 from the immunological test apparatus 10.

In a case where either the first determination result or the second determination result is obtained in the determination of step ST120 (NO in step ST130 and YES in step ST150), it is possible to input a test stop instruction through the touch panel 19. Here, in a case where the test stop instruction is input (YES in step ST160), as in the case where the first and second determination results are obtained in the determination of step ST120 (YES in step ST130), the first test record 90A is transmitted from the information output unit 86 to the information processing server 11 (step ST140). Then, the test is stopped by the main controller 80.

On the other hand, in a case where the test stop instruction is not input (NO in step ST160) and the elapsed time TP does not exceed the set time TS (0<TP≤TS, NO in step ST170), the process returns to step ST100 to continue the test. Also in a case where neither the first determination result nor the second determination result is obtained in the determination of step ST120 (NO in both steps ST130 and ST150) and the elapsed time TP does not exceed the set time TS (0<TP≤TS, NO in step ST170), the process returns to step ST100 to continue the test.

Figure 23:
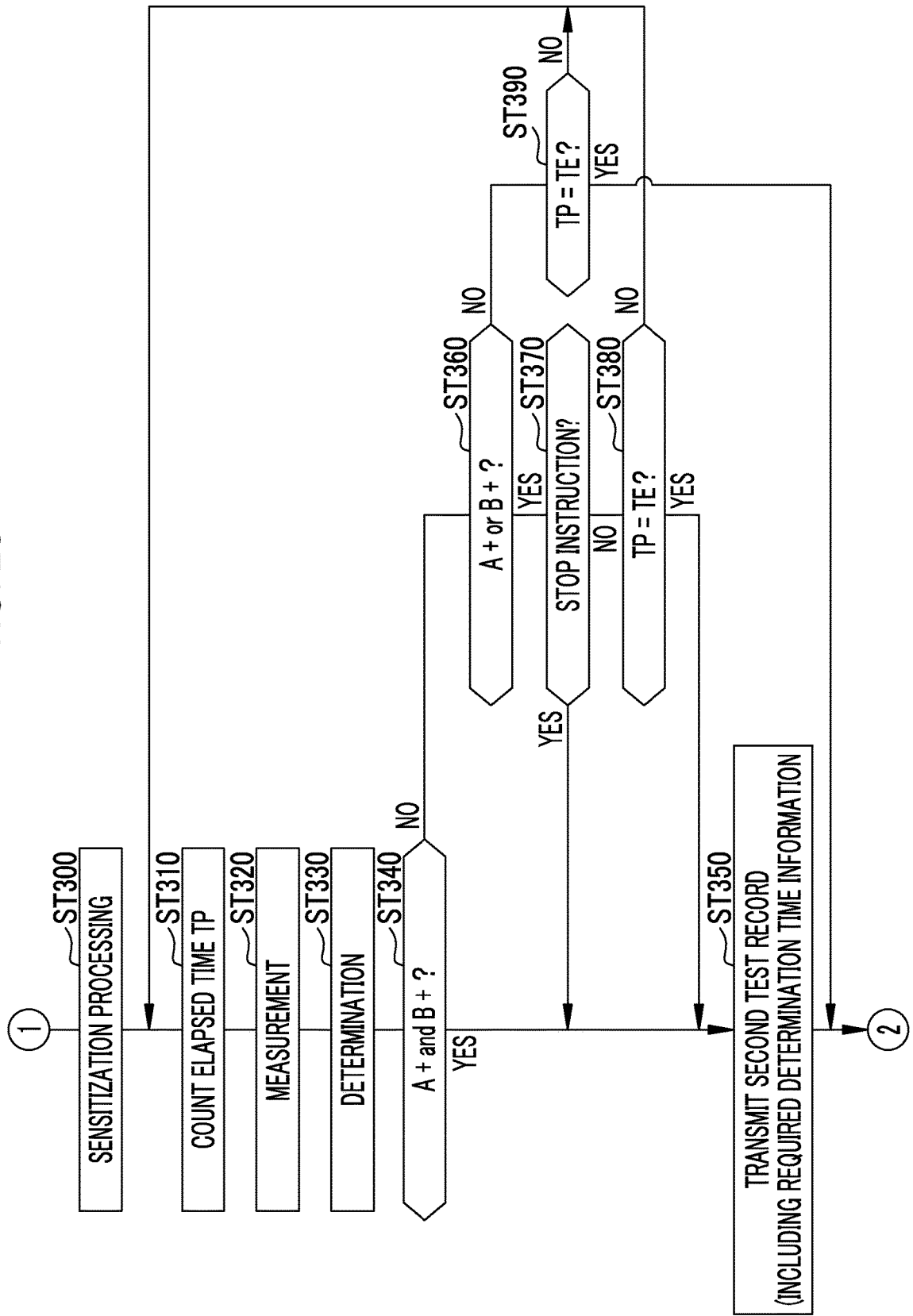
FIG. 23 is a flowchart showing the procedure of processing of the immunological test apparatus.

In a case where either the first determination result or the second determination result is obtained and the test stop instruction is not input (NO in step ST130, YES in step ST150, and NO in step ST160) and a case where neither the first determination result nor the second determination result is obtained (NO in both steps ST130 and ST150), in a case where the elapsed time TP exceeds the set time TS (TP>TS, YES in step ST170), sensitization processing is performed as shown in step ST300 in FIG. 23.

Specifically, a driving command is output from the main controller 80 to the driving controller 83, and the chemical solution spreading unit 47 (motor 55) is driven by the driving controller 83 that has received the driving command. By the driving of the chemical solution spreading unit 47, the reducing solution pot 37 is crushed by the first pressing piece 61 of the first pressing unit 56, and the reducing solution SR is spread to the test region 31. Then, the sensitizing solution pot 38 is crushed by the second pressing piece 64 of the second pressing unit 57, and the sensitizing solution SSE is spread to the test region 31. This increases the density of coloration of the reagent.

Thereafter, as in steps ST100 to ST120 in FIG. 22, counting of the elapsed time TP (step ST310, timing step), measurement (step ST320), and determination (step ST330) are performed.

In a case where both the first determination result and the second determination result are obtained in the determination of step ST330 (YES in step ST340), the second test record 90B is transmitted from the information output unit 86 to the information processing server 11 (step ST350, information output step). In this case, the main controller 80 ends the test without waiting for the elapsed time TP to become the time TE. The user can take out the cartridge 15 from the immunological test apparatus 10.

In a case where either the first determination result or the second determination result is obtained in the determination of step ST330 (NO in step ST340 and YES in step ST360), it is possible to input the test stop instruction through the touch panel 19 in the same manner as before the sensitization processing is performed. Here, in a case where the test stop instruction is input (YES in step ST370), as in the case where the first and second determination results are obtained in the determination of step ST330 (YES in step ST340), the second test record 90B is transmitted from the information output unit 86 to the information processing server 11 (step ST350, information output step). Also in this case, the main controller 80 ends the test without waiting for the elapsed time TP to become the time TE.

On the other hand, in a case where the test stop instruction is not input (NO in step ST370) and the elapsed time TP is not the time TE (TP≠TE, NO in step ST380), the process returns to step ST310 to continue the test. Also in a case where neither the first determination result nor the second determination result is obtained or either the first determination result or the second determination result is not obtained in the determination of step ST330 (NO in both steps ST340 and ST360) and the elapsed time TP is not time TE (TP≠TE, NO in step ST390), the process returns to step ST310 to continue the test.

In a case where the test stop instruction is not input (NO in step ST380) and the elapsed time TP becomes the time TE and a determination result indicating that the measurement has ended correctly is output from the determination unit 82 (YES in step ST380), the second test record 90B is transmitted from the information output unit 86 to the information processing server 11 (step ST350, information output step).

On the other hand, in a case where neither the first determination result nor the second determination result is obtained or either the first determination result or the second determination result is not obtained in the determination of step ST330 (NO in both steps ST340 and ST360) and the elapsed time TP becomes the time TE (TP=TE) and a determination result indicating that the measurement has ended correctly is output from the determination unit 82 (YES in step ST390), the main controller 80 ends the test. In this case, the test record 90 is not transmitted from the information output unit 86 to the information processing server 11.

Figure 24:
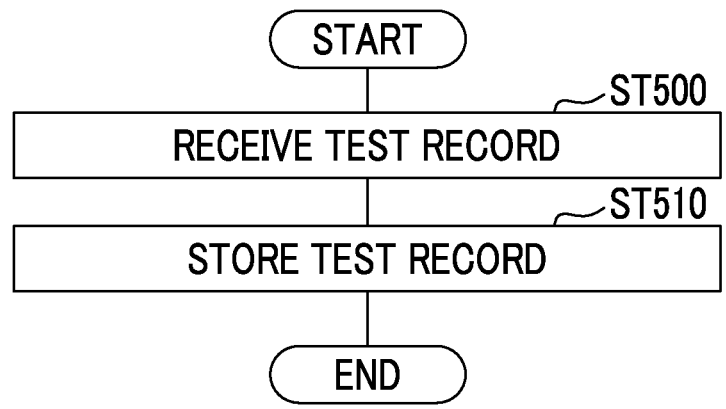
FIG. 24 is a flowchart showing the procedure of processing of the information processing server.

As shown in FIG. 24, in the information processing server 11, the test record 90 transmitted from the information output unit 86 of the immunological test apparatus 10 through the network 12 is received by the reception unit 120 (step ST500, reception step). The test record 90 is output from the reception unit 120 to the information management unit 121, and is stored in the test record table 116 by the information management unit 121 (step ST510).

Figure 25:
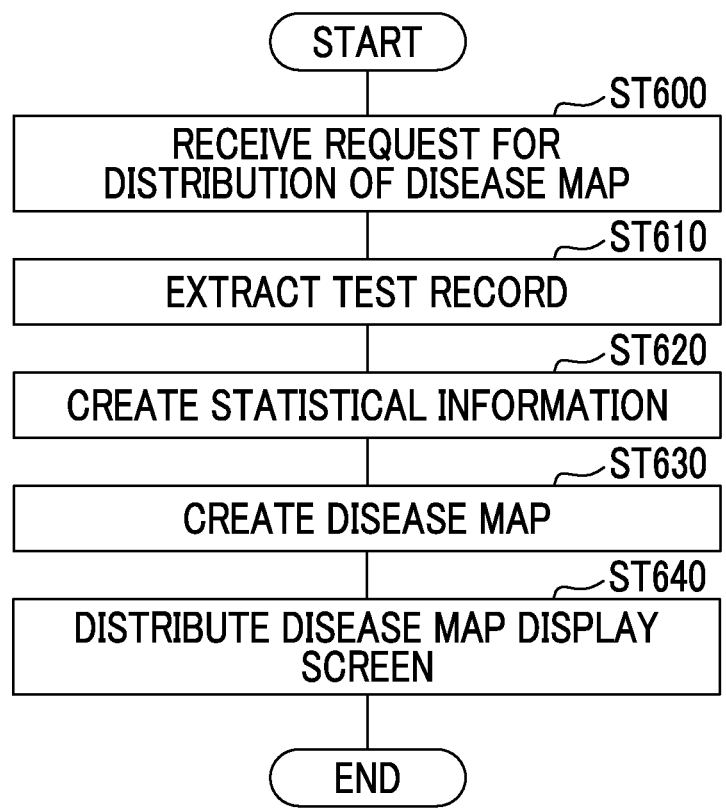
FIG. 25 is a flowchart showing the procedure of processing of the information processing server.

The user operates the client terminal 13 to access the information providing site, and transmits a request for distribution of the disease map 136 to the information processing server 11 through the client terminal 13. As shown in FIG. 25, in the information processing server 11, the request for distribution of the disease map 136 transmitted from the client terminal 13 through the network 12 is received by the request receiving unit 122 (step ST600). The request for distribution of the disease map 136 is output from the request receiving unit 122 to the statistical information creation unit 123.

In a case where the request for distribution of the disease map 136 is received, an extraction command is output from the statistical information creation unit 123 to the information management unit 121. As a result, the test record 90 whose reception date and time is within a predetermined period is extracted from the test record table 116 (step ST610). The extracted test record 90 and the installation location information 117 are output from the information management unit 121 to the statistical information creation unit 123.

In the statistical information creation unit 123, the statistical information 130 is created based on the test record 90 and the installation location information 117 (step ST620, statistical information creation step). The statistical information 130 is output from the statistical information creation unit 123 to the map creation unit 124.

The map creation unit 124 creates the disease map 136 based on the statistical information 130 (step ST630). The disease map 136 is output from the map creation unit 124 to the screen output controller 125.

The screen output controller 125 generates the disease map display screen 135 based on the disease map 136. The disease map display screen 135 is distributed from the screen output controller 125 to the client terminal 13 of the distribution request source (step ST640). In the client terminal 13, under the control of the browser controller 110, the disease map display screen 135 is displayed on the web browser of the display unit of the input and output device 104L.

As described above, since the immunological test apparatus 10 outputs the required determination time information 92 regarding the required determination time, which is taken until the determination result indicating that influenza virus is present in the sample SSP is obtained, so as to be associated with the determination result information 91, it is possible to make effective use of the required determination time to prevent the spread of influenza infection.

The immunological test apparatus 10 starts the sensitization processing in a case where at least one of the first determination result indicating that A type influenza virus is present in the sample SSP or the second determination result indicating that B type influenza virus is present in the sample SSP is not obtained during a period from the start of the test to the set time TS. Accordingly, in a case where there is only a very small amount of influenza virus in the sample SSP and the density of coloration of the reagent is very low, that is, only in a case where it is certainly necessary to increase the density of coloration of the reagent, the sensitization processing can be performed.

Since the information output unit 86 outputs, as the required determination time information 92, at least information indicating that the elapsed time TP exceeds the set time TS, and further, information indicating that the sensitization processing has been performed, distinction as to whether the patient, from who the sample SSP is collected, is an early stage patient or a middle stage patient can be made reliably based on the required determination time information 92. Therefore, it is possible to improve the reliability of the statistical information 130 created according to the distinction, and therefore, the disease map 136.

Since the information output unit 86 outputs the required determination time information 92 only in a case where the sensitization processing is performed, it is not necessary to perform excessive processing in a case where the sensitization processing is not performed. In addition, as there is no required determination time information 92, the data capacity of the first test record 90A can be smaller than that of the second test record 90B.

Since the information output unit 86 transmits the test record 90 to the information processing server 11 through the network 12, transmission of the test record 90 does not require much time and effort. The test records 90 from the plurality of immunological test apparatuses 10 can be easily accumulated in the information processing server 11.

Since the information output unit 86 transmits the test record 90 to the information processing server 11 for each test, the latest test record 90 is always accumulated in the information processing server 11. Therefore, since it is possible to ensure the immediacy of the statistical information 130, and therefore, the disease map 136, it is possible to notify the user of the epidemic situation of the ongoing influenza.

The output form of the test record 90 is not limited to the form of transmission through the network 12 described above. For example, the test record 90 may be written into a removable medium, such as a universal serial bus (USB) memory. Alternatively, instead of transmitting the test record 90 for each test, the test record 90 for a predetermined period, for example, one day, may be stored in the immunological test apparatus 10, and the entire test record 90 of the day may be transmitted at the end of the test of one day.

The information processing server 11 creates the statistical information 130 of influenza patients based on the required determination time information 92, the determination result information 91, and the installation location information 117, creates the disease map 136 by expressing the number of influenza patients for each area on a map, and outputs this as the disease map display screen 135. Therefore, particularly in the case of the disease map 136B of early stage patients, the user can predict how the epidemic situation of influenza will change from the disease map display screen 135 at the early stage of influenza infection. As a result, it is possible to take effective measures to prevent the spread of infection.

Since the information processing server 11 creates and outputs the disease map 136A of middle stage patients in addition to the disease map 136B of early stage patients, it is possible to obtain information, which cannot be known with a single disease map, by comparing the disease maps 136A and 136B with each other. For example, in a prefecture where the number of first test records 90A (the number of middle stage patients) is larger than the number of second test records 90B (the number of early stage patients), it can be predicted that the epidemic of influenza has peaked and is going down. Conversely, in a prefecture where the number of second test records 90B (the number of early stage patients) is larger than the number of first test records 90A (the number of middle stage patients), it can be predicted that there is a sign that influenza will spread from now on. In a prefecture where the number of first test records 90A (the number of middle stage patients) is approximately the same as the number of second test records 90B (the number of early stage patients), it can be predicted that the epidemic of influenza is heading to a peak.

The statistical information creation unit 123 may create at least the statistical information 130B of early stage patients of influenza, and the map creation unit 124 may create at least the disease map 136B by expressing the number of early stage patients of influenza for each area on a map.

Figures 26, 27:
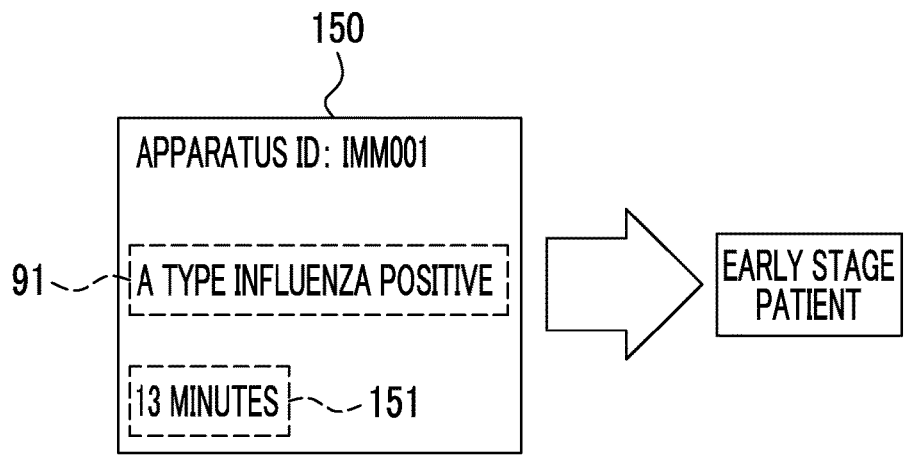
FIG. 26 is a diagram showing another example of the test record.
FIG. 27 is a diagram showing a statistical information display screen.

As in a test record 150 shown in FIG. 26, the required determination time itself may be used as required determination time information 151. In this case, the set time TS may be grasped on the information processing server 11 side, and whether to perform the sensitization processing may be determined according to whether or not the required determination time exceeds the set time TS.

In FIG. 26, the required determination time is "13 minutes", which exceeds 12 minutes that is the set time TS in this example. Therefore, it can be seen that the test record 150 has been subjected to the sensitization processing and the patient from which the sample SSP has been collected is an early stage patient.

In the above embodiment, the immunological test apparatus 10 has been described as having a function of performing sensitization processing. However, the present invention is not limited thereto. The present invention can also be applied to an immunological test apparatus that does not have the function of performing sensitization processing.

In the case of the immunological test apparatus having no function of performing sensitization processing, a required determination time is output as exemplified in FIG. 26 as the required determination time information. Then, a threshold value of the required determination time is set in advance on the information processing server 11 side, and determination as a middle stage patient is made in a case where the required determination time of the required determination time information is equal to or less than the threshold value, and determination as an early stage patient is made in a case where the required determination time of the required determination time information is larger than the threshold value.

The immunological test apparatus 10 having a function performing sensitization processing exemplified in the above embodiment and an immunological test apparatus having no function of performing sensitization processing may be mixed.

The management entity of the information processing server 11 is not limited to the sales company of the immunological test apparatus 10. A public organization such as the Ministry of Health, Labor and Welfare may manage the information processing server 11. The disease map 136 may be widely open to general users as well as users having the access authority of the information providing site.

The screen output controller 125 may output a statistical information display screen 160 shown in FIG. 27 or 28 in addition to or instead of the disease map display screen 135. The statistical information display screen 160 shown in FIG. 27 displays the statistical information 130 obtained by integrating the statistical information 130A and 130B shown in FIGS. 17 and 18. A scroll bar 161 for scrolling a non-displayed portion is provided in the statistical information 130. The statistical information display screen 160 shown in FIG. 28 displays the degree of magnitude of the number of middle stage patients and the number of early stage patients in a city, a prefecture to which the city belongs, an area to which the prefecture belongs, and the whole country. Thus, the epidemic situation of influenza can be predicted based on the statistical information 130 not based on the disease map 136. The epidemic situation of influenza can also be predicted by displaying the degree of magnitude of the number of patients instead of specific numbers as in the statistical information 130 shown in FIG. 28.

In the above embodiment, an example has been described in which measurement and determination are repeated until the elapsed time TP reaches the time TE after the sensitization processing. However, measurement and determination after the sensitization processing may be performed only once.

The hardware configuration of a computer, which forms the information processing apparatus of the present invention, can be modified in various ways. For example, in order to improve the processing capacity or reliability, the information processing apparatus can also be formed by a plurality of computers that are separated from each other as hardware. Specifically, the functions of the reception unit 120 and the information management unit 121 and the functions of the request receiving unit 122, the statistical information creation unit 123, the map creation unit 124, and the screen output controller 125 in the above embodiment can be distributed on two computers. In this case, the two computers form the information processing apparatus.

In the above embodiment, an example has been described in which the map creation unit 124 and the screen output controller 125 are provided in the information processing server 11 that is an information processing apparatus. However, the screen output controller 125 or the map creation unit 124 and the screen output controller 125 may be provided in the client terminal 13. In a case where the screen output controller 125 is provided in the client terminal 13, the information processing server 11 transmits the disease map 136 created by the map creation unit 124 to the client terminal 13. In a case where the map creation unit 124 and the screen output controller 125 are provided in the client terminal 13, the information processing server 11 transmits the statistical information 130 created by the statistical information creation unit 123 to the client terminal 13.

The immunological test apparatus 10 may be operated as an information processing apparatus. In this case, for example, each unit such as the reception unit 120 or the statistical information creation unit 123 constructed in the CPU 102S of the information processing server 11 of the embodiment described above is constructed in the main controller 80 of one of the plurality of immunological test apparatuses 10. In this case, the immunological test apparatus 10 operating as an information processing apparatus receives the test record 90 transmitted from the other immunological test apparatuses 10 and the test record 90 output from its own information output unit 86 by the reception unit 120.

In addition to or instead of the client terminal 13, the disease map display screen 135 may be transmitted to the immunological test apparatus 10. In this case, the request for distribution of the disease map 136 is input through the touch panel 19, and the disease map display screen 135 is displayed on the touch panel 19.

Thus, the hardware configuration of a computer can be appropriately changed according to the required performance, such as processing capacity, safety, or reliability. Needless to say, in order to ensure the safety or reliability, an AP, such as the operation program 115, may be duplicated or may be stored in a plurality of storage devices in a distributed manner, without being limited to hardware.

In the embodiment described above, a form is exemplified in which each screen, such as the disease map display screen 135, is distributed from the screen output controller 125 to the client terminal 13 in the form of screen data for web distribution. However, an AP for displaying each screen may be installed on the client terminal 13, and an instruction to cause the AP to display each screen may be output from the screen output controller 125.

The output form of the statistical information 130 or the disease map 136 is not limited to the disease map display screen 135 or the statistical information display screen 160 exemplified in the embodiment described above, and print output of the statistical information 130 or the disease map 136 to a paper medium or file output using e-mail and the like are included.

In each of the embodiments described above, the hardware structures of processing units for executing various kinds of processing, such as the main controller 80 corresponding to the timing unit, the driving controller 83, the information output unit 86, the reception unit 120, the information management unit 121, the request receiving unit 122, the statistical information creation unit 123, the map creation unit 124, and the screen output controller 125, are various processors shown below. The various processors include a central processing unit (CPU) that is a general-purpose processor that executes software (program) to function as various processing units, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor. As an example of configuring a plurality of processing units using one processor, first, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

In addition, the hardware structure of these various processors is an electrical circuit (circuitry) in the form of a combination of circuit elements, such as semiconductor elements.

From the above description, it is possible to grasp the invention shown in the following supplementary items.

[Supplementary Item 1]

An immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement, the apparatus comprising: a timing processor that counts an elapsed time from start of a test; and an information output processor that outputs required determination time information regarding a required determination time, which is the elapsed time taken until a determination result indicating that the test substance is present in the sample is obtained, so as to be associated with information of the determination result.

[Supplementary Item 2]

An information processing apparatus connected, through a network, to an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement, the information processing apparatus comprising: a reception processor that receives required determination time information regarding a required determination time, which is an elapsed time of a test taken until a determination result indicating that the test substance is present in the sample is obtained from start of the test, and information of the determination result from the immunological test apparatus through the network; and a statistical information creation processor that creates statistical information of early stage patients, who are patients at an early stage of infection of an infectious disease, based on the required determination time information, the determination result information, and installation location information regarding an installation location of the immunological test apparatus.

In the present invention, it is also possible to appropriately combine the above-described various embodiments or various modification examples. Without being limited to the embodiments described above, it is needless to say that various configurations can be adopted without departing from the scope of the present invention. For example, the test substance is not limited to influenza virus. The test substance may be adenovirus, rotavirus, hepatitis virus, pneumococci, and the like. In addition to the program, the present invention also extends to a storage medium that stores the program.

EXPLANATION OF REFERENCES

2: information processing system
10: immunological test apparatus
10A: apparatus main body
11: information processing server (information processing apparatus)
12: network
13: client terminal
15: cartridge
15A: case
16: opening
17: lid
18: cartridge loading unit
19: touch panel
20: dropping port
21: label
30: carrier
31: test region
32, 33: observation window
35: solution feeding pad
36: solution absorbing pad
37: reducing solution pot
38: sensitizing solution pot
45: guide rail
46: measurement unit
47: chemical solution spreading unit
50: light source
51: imaging element
55: motor
56 first pressing unit
57: second pressing unit
60, 63: first and second arms
60A: shaft
61, 64: first and second pressing piece
62, 65: first and second cams
80: main controller (timing unit)
81: measurement controller
82: determination unit
83: driving controller
84: display controller
85: instruction receiving unit
86: information output unit
90, 150: test record
90A, 90B: first and second test records
91: determination result information
92, 151: required determination time information
100, 100S: storage device
101: memory
102, 102L, 102S: CPU
103: communication unit
104, 104L: input and output device
105: data bus
110: browser controller
115: operation program
116: test record table
116A, 116B: first and second test record table
117: installation location information
120: reception unit
121: information management unit
122: request receiving unit
123: statistical information creation unit
124: map creation unit
125: screen output controller (output controller)
130, 130A, 130B: statistical information
135: disease map display screen
136, 136A, 136B: disease map
137, 137A, 137B: legend
140: menu
160: statistical information display screen
161: scroll bar
A, B: test line
C: control line
SSP: sample
SR: reducing solution
SSE: sensitizing solution
TP: elapsed time
TS: set time
TE: time taken for sample to reach control line
ST100 to S170, ST300 to ST390, ST500, ST510, ST600 to ST640: step

What is claimed is:

1. An immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement, the apparatus comprising:
 a timing unit that counts an elapsed time from start of a test, wherein a timing of the start of the test is a timing at which the sample is dropped onto the carrier; and
 an information output unit that outputs required determination time information regarding a required determination time, which is the elapsed time taken until a determination result indicating that the test substance is present in the sample is obtained, so as to be associated with information of the determination result.

2. The immunological test apparatus according to claim 1, further comprising:
 a chemical solution spreading unit that performs sensitization processing in which a chemical solution for sensitizing the coloration state is spread onto the carrier; and
 a driving controller that controls driving of the chemical solution spreading unit, wherein, in a case where a determination result indicating that the test substance is present in the sample is not obtained during a period from the start of the test to a set time set in advance, the driving controller drives the chemical solution spreading unit to start the sensitization processing, and the information output unit outputs, as the required determination time information, at least information indicating that the elapsed time exceeds the set time.

3. The immunological test apparatus according to claim 2, wherein the information output unit outputs the required determination time information only in a case where the elapsed time exceeds the set time and the sensitization processing is performed.

4. The immunological test apparatus according to claim 2, wherein the information indicating that the elapsed time exceeds the set time is information indicating that the sensitization processing has been performed.

5. The immunological test apparatus according to claim 1, wherein the information output unit transmits the required determination time information and the determination result information to an information processing apparatus connected through a network.

6. The immunological test apparatus according to claim 5, wherein the information output unit transmits the required determination time information and the determination result information for each test.

7. An operation method of an immunological test apparatus that receives a carrier holding a reagent, which is combined with a test substance as an antigen of an infectious disease to be colored, and having a sample dropped thereon, measures a state of the coloration, and determines whether or not the test substance is present in the sample based on a result of the measurement, the operation method comprising:

a timing step of counting an elapsed time from start of a test, wherein a timing of the start of the test is a timing at which the sample is dropped onto the carrier; and an information output step of outputting required determination time information regarding a required determination time, which is the elapsed time taken until a determination result indicating that the test substance is present in the sample is obtained, so as to be associated with information of the determination result.

* * * * *